United States Patent
Tidwell et al.

(10) Patent No.: US 9,382,572 B2
(45) Date of Patent: Jul. 5, 2016

(54) METHODS OF DETERMINING BIOCIDE EFFICACY OR MECHANISM OF ACTION USING FLOW CYTOMETRY

(71) Applicant: Ecolab USA Inc., Eagan, MN (US)

(72) Inventors: Timothy J. Tidwell, Houston, TX (US); Zachary Richard Broussard, The Woodlands, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 14/466,232

(22) Filed: Aug. 22, 2014

(65) Prior Publication Data

US 2015/0056648 A1    Feb. 26, 2015

Related U.S. Application Data

(60) Provisional application No. 61/869,388, filed on Aug. 23, 2013.

(51) Int. Cl.
*C12Q 1/18* (2006.01)
*G01N 15/14* (2006.01)

(52) U.S. Cl.
CPC .............. *C12Q 1/18* (2013.01); *G01N 15/1459* (2013.01)

(58) Field of Classification Search
CPC ................................................. G01N 15/1459
See application file for complete search history.

(56) References Cited

U.S. PATENT DOCUMENTS

2011/0207786 A1 * 8/2011 Callahan et al. .............. 514/373
2013/0052645 A1   2/2013 Scott

OTHER PUBLICATIONS

Boye et al. J of General Microbiology, 1983, 129:973-980.*
Jepras et al. Antimicrobial Agent and Chemotherapy, 1997, 41(9):2001-2005.*
Kramer et al. NACE corrosion 2008 conference & expo, pp. 1-14.*
Al-Juboori, R. A., et al., "Biofouling in RO System: Mechanisms, Monitoring and Controlling," Desalination, 2012, pp. 1-23, vol. 302.
Binet, M. T., et al., "Rapid Flow Cytometric Method for the Assessment of Toxic Dinoflagellate Cyst Viability," Marine Environmental Research, 2006, pp. 247-260, vol. 62.
Davison, W. M., et al., "Spatial and Temporal Patterns of Biocide Action Against *Staphylococcus epidermidis* Biofilms," Antimicrobial Agents and Chemotherapy, Jul. 2010, pp. 2920-2927, vol. 54, No. 7.
International Search Report and Written Opinion issued for PCT/US2014/052330, dated Dec. 1, 2014, 15 pages.
Sheppard, F. C., et al., "Flow Cytometric Analysis of Chlorhexidine Action," FEMS Microbiology Letters, 1997, pp. 283-288, vol. 154.
Simoes, M. et al., "Validation of Respirometry as a Short-Term Method to Assess the Efficacy of Biocides," Biofouling, 2005, pp. 9-17, vol. 21, No. 1.

* cited by examiner

*Primary Examiner* — Bin Shen
(74) *Attorney, Agent, or Firm* — Senniger Powers LLP

(57) ABSTRACT

Disclosed are methods of determining biocide efficacy using flow cytometry. The methods can be used to determine the synergy between at least two biocides.

20 Claims, 27 Drawing Sheets

METHODS OF DETERMINING BIOCIDE EFFICACY OR MECHANISM OF ACTION USING FLOW CYTOMETRY

CROSS-REFERENCE TO RELATED APPLICATIONS

This application claims the benefit of U.S. Provisional Patent Application Ser. No. 61/869,388, filed Aug. 23, 2013, the entirety of which is herein incorporated by reference.

FIELD OF THE INVENTION

The present disclosure relates generally to methods of determining biocide efficacy or mechanism of action using flow cytometry.

BACKGROUND OF THE INVENTION

Oilfield systems are subjected to increased risks associated with microbial control including: H2S production, microbial influenced corrosion (MIC) and biofouling. When MIC is suspected in a system, the main area of concern becomes the biofilm, or sessile organisms, on the surface of the pipeline. It is widely recognized, within the industry, that in order to be effective at controlling the bacteria within a system there should be a focus on minimizing biofilm regrowth kinetics following treatment (sessile control) in addition to providing sufficient planktonic kill. While use of biocides such as tetrakis-(hydroxymethyl) phosphonium sulfate, glutaraldehyde, and quaternary ammonium compounds are used to delay the regrowth kinetics of biofilms, there is an increased need to identify biocides or combination of biocides that provide the most efficient performance means for microbial kill and biofilm control, and in particular, penetration and delay in the regrowth kinetics of biofilms.

Current biocide performance testing relies on classical microbiological culturing techniques and other non-culture based methods such as ATP photometry and fluorescence microscopy. For field monitoring of microorganism growth in oilfield systems, the standard test method is the NACE International Standard Test Methods, which is fully incorporated herein by reference. These methods include membrane filtration methods for assessing bacterial populations, culturing by serial dilution, and alternative sulfate reducing bacteria (SRB) media growth methods. These methods have drawbacks due to delays in culturing oilfield bacteria that can take as long as two to four weeks to incubate and grow, thereby delaying biocide performance optimization. Non-culture based methods such as ATP photometry reduce the time for biocide optimization, but do not always measure all microbes in a particular isolation because these methods cannot identify microbes that are dying, but have not lysed or the membrane are still intact.

Accordingly, despite the available technologies, there remains a need for measuring biocide performance and synergies for efficient use in oilfield and other applications (e.g., food industry, paper industry, water purification, waste water treatment, etc.). This method would provide quick analysis of bacterial populations in particular isolates (e.g., oil field samples), absolute quantification of dead microbes, and insight into biocidal mechanisms of action via amount of time to apply the biocide, concentration of the biocide and preferred combinations of different biocides to identify chemical/biological synergies.

SUMMARY OF THE INVENTION

Presented herein is a method of measuring biocide efficacy using flow cytometry, the method comprising (a) contacting a medium with at least one biocide; (b) performing flow cytometry on the medium of step a); and (c) determining the mechanism of action or efficacy of the at least one biocide on a microorganism present in the medium based on step b). The medium can contain at least one microorganism wherein the at least one microorganism is prokaryotic or eukaryotic. The method can comprise contacting the medium with at least two biocides, which are compared for their mechanism of action or efficacy for the purpose of identifying synergy in controlling microorganisms in the medium. The method can further comprise contacting the microorganism with at least one selectivity agent to produce a labeled microorganism. The method can further comprise performing flow cytometry on the labeled microorganism and collecting spectral data for said microorganism. The method can further comprise defining one or more subsets of the microorganism based on the spectral data. The spectral data comprises at least one of forward scattering data, side scattering data, and fluorescence data, wherein at least a portion of the spectral data corresponds to a microorganism in a condition selected from the group consisting of viable, membrane-damaged, depolarized, and combinations thereof. The at least one selectivity agent can be selected from the group consisting of a cell-impermeable stain, a membrane potential stain, and combinations thereof wherein the medium comprises water, an oil and gas fluid, a food and beverage fluid, a medical fluid, or a combination thereof. The at least one biocide can be selected from the group consisting of aldehydes, dialdehydes, quaternary ammonium compounds, quaternary phosphonium compounds, halogens, and combinations thereof.

The present invention can further comprise a method of identifying biocide synergy using flow cytometry, the method comprising (a) contacting a first medium with a first biocide; (b) contacting a second medium with a second biocide; (c) performing flow cytometry on the first medium of step a) and the second medium of step (b); and (d) comparing the mechanism of action of the first biocide and second biocide on a microorganism present in the medium based on step c). The first medium and second medium can each contain a plurality of microorganisms, the method further comprising contacting each plurality of microorganisms with at least one selectivity agent to produce at least one plurality of labeled microorganisms. The medium can comprise water, an oil and gas fluid, a food and beverage fluid, a medical fluid, or a combination thereof. The at least two biocides can be selected from the group consisting of aldehydes, dialdehydes, quaternary ammonium compounds, quaternary phosphonium compounds, halogens, and combinations thereof.

The present invention can further be directed to a method of monitoring microorganism growth in a medium, the method comprising (a) contacting a medium with at least one biocide; (b) performing flow cytometry on the medium of step a); (c) determining the mechanism of action or efficacy of the at least one biocide on a microorganism present in the medium based on step b); (d) repeating steps (a) to (c) at a later time; (e) comparing results of microorganism growth at step (c) with step (d) to determine if biocide of step (a) is effective in controlling growth of the microorganism in the medium. The medium can contain at least one microorganism. The method can further comprise using alternative biocides in controlling growth of microorganism based upon results in step (e).

DETAILED DESCRIPTION

Figure 1:
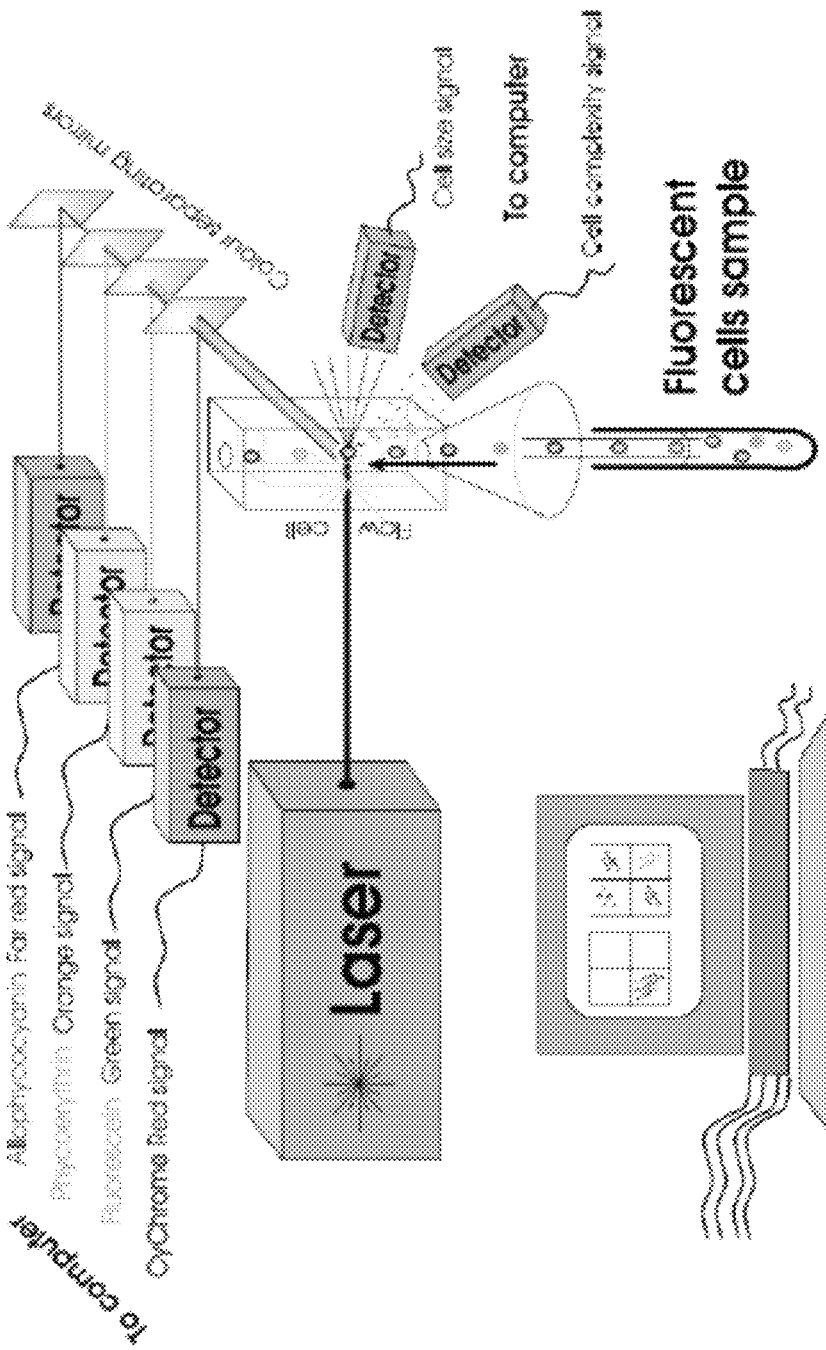
FIG. 1 depicts a schematic of flow cytometry.
Figure 2:
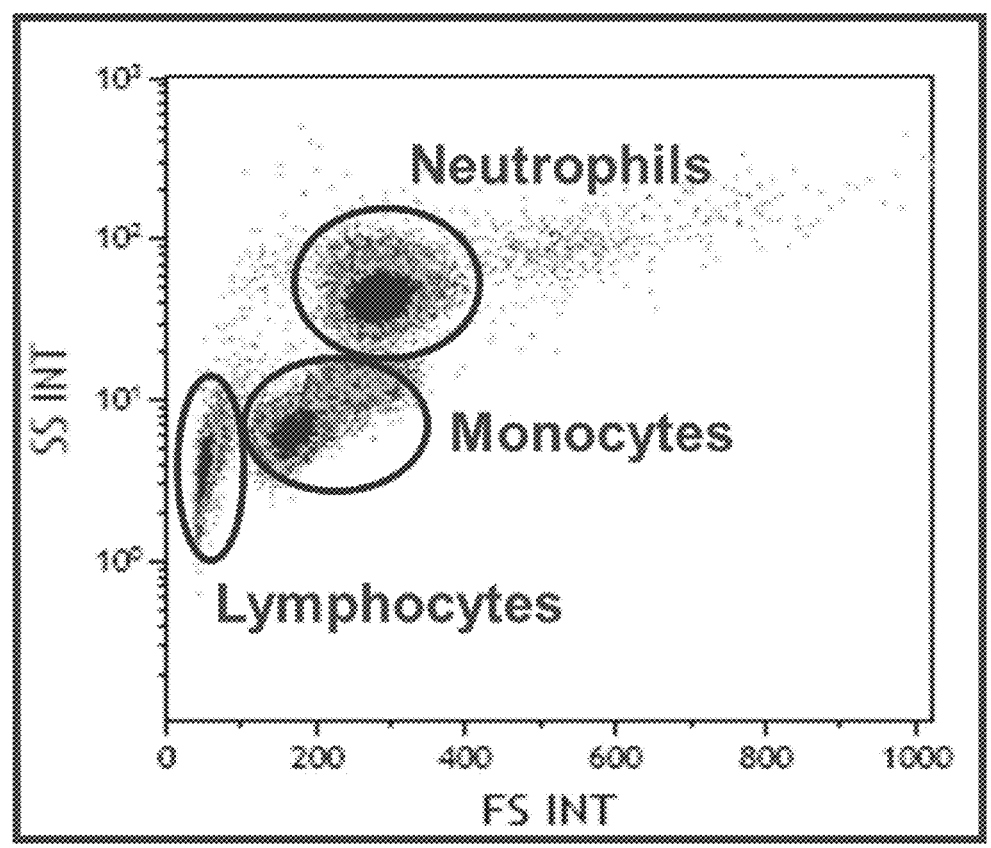
FIG. 2 depicts a representative flow cytometry output.

Disclosed herein is a method of using flow cytometry to measure biocide performance on controlling microorganism growth in mediums such as oil and gas fluids. The use of flow cytometry may not be able to differentiate microorganisms, but it provides the ability to measure how well and why a biocide works in a particular medium.

Flow cytometry is capable of providing insight into the mechanism of action of a biocide by monitoring the intensity of fluorescence emission from a selective binding agent of interest from a group of microorganisms of interest. If the selective binding agent of interest binds a species on the interior of the cell of interest, but is impermeable to the cell membrane, then an intense fluorescence emission corresponding to the selective binding agent of interest from a cell of interest is an indication that the cell membrane has been damaged in such a way as to allow the selective binding agent of interest to enter the interior of the cell of interest. If the selective binding agent of interest binds the exterior of a cell of interest selectively, dependent upon a certain condition of the cell of interest (such as the electrostatic charge of its cell membrane), then an intense fluorescence emission corresponding to the selective binding agent of interest from a cell of interest is an indication that the cell of interest possesses the certain condition. If the concentration of a selective binding agent of interest within or bound to a cell of interest is dependent upon a certain cellular condition, then flow cytometry is capable of determining the degree of the certain cellular condition within the cell of interest, because the fluorescence emission correlates to the degree of the certain cellular condition. If the certain cellular condition is related to the mechanism of action of a biocide of interest, then flow cytometry can help illuminate the mechanism of action.

Through the measurement of relative increases in fluorescence over an untreated control, the use of flow cytometry can provide insight into many physiological changes to the microorganism due to a biocide. For example, this method can provide overall dead and alive cell counts in a sample. Flow cytometry can provide information regarding the effect of the biocide on cell morphology and membrane integrity. The method can be used to study the effect of the biocide on overall cell metabolism vs. membrane potential. Biocide synergies can be identified using flow cytometry by combining particular chemistries of two or more biocides, and identifying their physiological mechanism of action to complement the other biocide in the treatment cocktail. For example, the method can identify one biocide that is efficient in altering cell membrane potential while a second biocide can be identified as effective in slowing or quashing cell metabolism. Using flow cytometry provides field scientists an ability to identify the most efficient biocide cocktails that optimize the biological action to control microorganism growth or regrowth. Flow cytometry can also be used to measure a biocide's effect on protein expression, measurement of DNA content and the replication ability of the microorganism. Also, flow cytometry can identify whether there is oxidative stress in the microorganism.

Finally, disclosed herein are methods for using flow cytometry to measure the effect of biocide concentration on microorganism control, timing of treatment on a microorganism population using a particular biocide or combination, and biological mechanisms of the biocide. The methods provide an ability to study biocides quickly as results can be generated within a couple of hours of field isolation of, for example, an oilfield sample. Through these efficient modes of measurement, better and more efficient biocides and combinations thereof will be identified thereby reducing environmental footprints and leading to more profitable processes for controlling microorganisms in the areas of oil/gas, food, textiles, waste management, water, health care, pest elimination, mining and paper.

1. DEFINITION OF TERMS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The term "biocide," as used herein, refers to a chemical used to control microorganisms by deterring, rendering harmless, or exerting a controlling effect on any harmful organism. Biocides are commonly used in medicine, agriculture, forestry, and industry. Biocidal substances and products are also employed as anti-fouling agents or disinfectants under other circumstances. Chlorine, for example, is used as a short-life biocide in industrial water treatment but as a disinfectant in swimming pools. Many biocides are synthetic, but a class of natural biocides, derived from, e.g., bacteria and plants, includes *Brassica oleracea, Brassica oleracea gemmifera*, and *Clostridium botulinum* bacteria.

The term "depolarization" or "depolarized," as used herein, refers to a cell that has decreased proton motive force, in some cases by virtue of arrest of oxidative phosphorylation.

The term "depolarizing," as used herein, refers to a cell that is between a viable state and a depolarized state.

The term "membrane damage" or "membrane-damaged," as used herein, refers to mechanical damage to the cytoplasmic membrane of a cell, which allows cell-impermeable molecules to enter and exit.

The term "membrane damage and depolarization" or "membrane-damaged and depolarized," as used herein, refers to a combination of membrane damage and depolarization, where the cell is irreparably damaged.

The term "non-culturable microorganisms," as used herein, refers to a microorganism that does not grow under normal culturing conditions. Examples of non-culturable microorganisms include, but are not limited to, pseudo-senescent cells or somnicells (sleeping cells) that can exist in cryptobiotic dormant, moribund, or latent states, in which the cells will not form colonies on nutrient media but will give a viable direct count via fluorescent viability stains.

The term "synergy" or "synergistic effect," as used herein, refers to the cooperative action between one biocide and a second biocide. The synergistic relationship is present in that the cooperative action of the combined biocide with another biocide yields or is predicted to yield a total effect that is greater than the sum of the effects of the first biocide or the second biocide taken separately.

The term "viable," as used herein, refers to a cell that is anionically charged with an intact membrane.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

2. USE OF A FLOW CYTOMETER TO MEASURE PERFORMANCE OF A BIOCIDE ON MICROORGANISM

Disclosed herein is a method for using flow cytometry to measure biocide efficacy for control of microorganisms in a medium. When a chemical inhibitor such as a biocide is desired to control microbial activity in a medium, it is necessary to select an effective chemical agent that is compatible with the fluids and components in the medium or system such as oil/gas fields. On-site dose response testing can be a guide for selecting biocides. The goal is to match test conditions to those prevailing in the medium under scrutiny.

Accordingly, the method can include contacting a medium with at least one biocide, performing flow cytometry on the medium, and determining the mechanism of action or efficacy of the at least one biocide on a microorganism based upon results of the flow cytometry. The method provides a rapid test that provides an accurate insight into absolute microbial kill and a means to differentiate the kill mechanism. The method further can comprise examination of biocide chemistry and determination of the biological mechanism of action via use of the flow cytometer on microorganism sampling from a medium. The method can apply to analyzing 1 or more, 2 or more, 3 or more, 4 or more, 5 or more, 6 or more, 7 or more, 8 or more, 9 or more, or 10 or more biocides.

The method has several advantages over existing methods, such as culture-based methods and ATP photometry. The method involves an automated quantification of individual species as opposed to existing methods that use direct plate counts and fluorescence microscopy, which involve manual counting of individual species. Culture-based methods can take as many as 14 to 28 days to complete, whereas the method can be completed within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. Culture-based methods are limited to only microorganisms that are culturable, whereas the methods disclosed herein can function with culturable and non-culturable microorganisms. Culture-based and ATP photometry methods can be used in the quantification of live microorganisms but cannot be used to provide insight into the biocidal mechanism, whereas the methods disclosed herein provide absolute quantification of live microorganisms and insight into the biocidal mechanism. Data from culture-based methods are typically represented in $\log_{10}$ increments (unless triplicate bottles are inoculated), whereas the methods disclosed herein provide continuous data. The method provides absolute quantification of live microorganisms and provides insight into biocidal mechanism as described below.

a. Mechanism of Action

The method of using flow cytometry to measure performance of a biocide can further be used to collect spectral data for the labeled microorganism that corresponds to a microorganism in a condition or physiological conditions such as "viable," "membrane-damaged," "depolarized," or combinations thereof. A "viable" cell refers to a cell that is anionically charged with an intact membrane. A "membrane damaged" cell has mechanical damage to the cytoplasmic membrane which allows cell-impermeable molecules to enter and exit. A "depolarized" cell has a decrease in proton motive force by arrest of oxidative phosphorylation. A "membrane damaged and depolarized" cell has a combination of membrane damage to the cytoplasmic membrane which allows cell-impermeable molecules to enter and exit and a decrease in proton motive force by arrest of oxidative phosphorylation. A "membrane damaged and depolarized" cell is irreparably damaged.

Biocides can act on a microorganism by one or more of the following mechanisms: (1) alteration of cell envelope, (2) inhibition of protein synthesis, (3) inhibition of nucleic acid synthesis, and (4) inhibition of a metabolic pathway. Biocides can act by destabilizing plasma membranes, causing cytoplasmic protein aggregation (loss of tertiary structure), inhibiting membrane-bound ATPase, collapsing membrane energy (ATP synthesis), inhibiting energy-dependent uptake of amino acids, discharging membrane potential, inhibiting DNA and RNA synthesis, inhibiting cell wall synthesis, inducing proton translocation, dissipating proton motive force, inhibiting uptake of amino acids, affecting active transport and oxidation of glucose, affecting activity of thiol-containing enzymes, ATPases, or glyceraldehyde-3-phosphate dehydrogenase, or intercalating with DNA.

The mechanism of action can be observed by using the method and applying biocides in varying concentrations. The relative populations of microorganisms in a condition or physiological condition can change as a function of concentration of biocide, which can provide insight into the mechanism of action.

The mechanism of action can be observed by using the method and applying biocides at varying time intervals. The relative populations of microorganisms in a condition or physiological condition can change as a function of time after applying biocide, which can provide insight into the mechanism of action.

One advantage of the method can be the ease with which the mechanism of action can be visualized by a user. In situations where the data are provided in a bivariate scatter plot, the evolution of the plot as the concentration or time are varied can provide information about the mechanism of action. Since different areas of the bivariate scatter plot correspond to different cellular conditions, two mechanisms of action that proceed via distinct cellular conditions can be visually distinguishable. In situations where the data are provided in bar graph form, the evolution of the size of the bars representing various microorganism conditions or physiological conditions as the concentration or time are varied can provide information about the mechanism of action. Since the size of the bars corresponds to the relative populations of different cellular conditions, two mechanisms of action that proceed via distinct cellular conditions can be visually distinguishable.

If the concentration of a selective binding agent of interest within or bound to a cell of interest is dependent upon a certain cellular condition, then flow cytometry is capable of determining the degree of the certain cellular condition within the cell of interest, because the fluorescence emission correlates to the degree of the certain cellular condition. If the certain cellular condition is related to the mechanism of action of a biocide of interest, then flow cytometry can help illuminate the mechanism of action.

b. Method of Measuring Efficacy of Biocide

The method of using flow cytometry to measure performance of a biocide can further comprise determining the efficacy of a biocide by studying the physiological state of a cell after exposure to the biocide. If the biocide is not very effective, the cells will sustain little if any damage. These cells will be viable and have an anionically charged intact membrane. If the biocide is effective, the cells can have membrane damage or become depolarized. The cells with membrane damage can have mechanical damage to the cytoplasmic membrane, which allows cell-impermeable molecules to enter and exit. The cells that are depolarized can have a decrease in proton motive force by arrest of oxidative phosphorylation. The biocide can cause irreparable damage by causing both membrane damage and depolarization of the cell, such as with cell lysis, which destroys the viability of the cell. The method disclosed herein allows the evaluation of the biocide efficacy based on the above physiological conditions.

c. Method of Identifying Biocide Synergies Using Flow Cytometry

The method of using flow cytometry to measure performance of a biocide can further comprise identifying biocide synergy between 2 or more, 3 or more, 4 or more, 5 or more, 6 or more, 7 or more, 8 or more, 9 or more, or 10 or more biocides without requiring the use of 2 or more, 3 or more, 4 or more, 5 or more, 6 or more, 7 or more, 8 or more, 9 or more, or 10 or more biocides together. The methods include a) contacting a first medium with a first biocide; b) contacting a second medium with a second biocide; performing flow cytometry on the first medium of step a) and the second medium of step b); and comparing the mechanism of action of the first biocide and second biocide based on step c). The first medium and second medium can each contain a plurality of microorganisms. The method can further include contacting each plurality of microorganisms with at least one selectivity agent to produce at least one plurality of labeled microorganisms.

The biocides can be added at a wt. ratio of 10:0, 9:1, 8:2, 7:3, 6:4, 5:5, 4:6, 3:7, 2:8, 1:9 or 0:10 of the first biocide to the second biocide.

The biocides can be added at a molar ratio of at least 1:1, at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, at least 30:1, at least 31:1, at least 32:1, at least 33:1, at least 34:1, at least 35:1, at least 36:1, at least 37:1, at least 38:1, at least 39:1, at least 40:1, at least 41:1, at least 42:1, at least 43:1, at least 44:1, at least 45:1, at least 46:1, at least 47:1, at least 48:1, at least 49:1, at least 50:1, at least 55:1, at least 60:1, at least 65:1, at least 70:1, at least 75:1, at least 80:1, at least 85:1, at least 90:1, at least 95:1, or at least 100:1.

The method can be further applied to identify and examine synergy between at least 2 biocides, at least 3 biocides, at least 4 biocides, at least 5 biocides, at least 6 biocides, at least 7 biocides, at least 8 biocides, at least 9 biocides, or at least 10 biocides. The method can include comparing at least 2 biocides, at least 3 biocides, at least 4 biocides, at least 5 biocides, at least 6 biocides, at least 7 biocides, at least 8 biocides, at least 9 biocides, or at least 10 biocides for their mechanism of action or efficacy for the purpose of identifying synergy in controlling microorganisms in the medium. The use of two or more biocides can provide a synergistic effect of controlling microorganisms. For example, a first biocide can alter the cell envelope, which would allow a second biocide to enter the cell, while a second biocide can have another mechanism of action, such as inhibiting protein synthesis, nucleic acid synthesis or a metabolic pathway. Because the cell envelope is altered or broken by the first biocide, the second biocide can enter the cell more easily and thus be more effective against the microorganism.

The method can be used to evaluate the synergies between biocide classes. The synergies between aldehydes and quaternary ammonium compounds; aldehydes and quaternary phosphonium compounds; halogens and cocodiamine; and THPS/cocodiamine/dialdehydes and combinations with inert chemistries can be evaluated. The methods disclosed herein can be used to determine the synergy of biocides didecyldimethylammonium chloride (DDAC) and tributyl tetradecyl phosphonium chloride (TTPC).

d. Method of Monitoring Microorganisms in a Medium Using Flow Cytometry

The method of using flow cytometry to measure performance of a biocide can further comprise monitoring microorganisms in any medium. The method of monitoring microorganism growth in a medium can comprise (a) contacting a medium with at least one biocide; (b) performing flow cytometry on the medium of step a); (c) determining the mechanism of action or efficacy of the at least one biocide on a microorganism present in the medium based on step b); (d) repeating steps (a) to (c) at a later time; (e) comparing results of microorganism growth at step (c) with step (d) to determine if biocide of step (a) is effective in controlling growth of the microorganism in the medium. The medium can contain more than 1, 2, 3, 4, 5, 6, 7, 8, 9, 10, 20, 30, 40, 50 or 100 different species of microorganisms. The method can be used to monitor microorganisms over 1, 2, 3, 4, 5, 6, 7, 8, 9, 10, 15, 20, or 25 hours or 1, 2, 3, 4, 5, 6, 7, 8, 9, 10, 20, or 40 days or 1, 2, 3, 4, 5, 6, 7, 8, 9, 10, 11, or 12 months. The method can further comprise using alternative biocide in controlling growth of the microorganism based upon the results in step (e).

3. BIOCIDE

The method disclosed above analyzes the effectiveness of biocides on controlling microorganism growth in a medium using flow cytometry. Biocides are used in the prevention of microbiological growth in all kinds of aqueous systems such as water, an oil and gas fluid, a food and beverage fluid, a medical fluid where the rapid determination of the amount of microorganisms present in such product is required for quality control or regulatory purposes. Biocides can also kill microorganisms as discussed below.

Biocides include oxidizing and non-oxidizing biocides. Oxidizing biocides are preferred due to their non-specificity, speed of kill, cost effectiveness, and ease of monitoring. Biocides can include aldehydes, quaternary ammonium compounds, quaternary phosphonium compounds, halogens, cocodiamine, tetrakis (hydroxymethyl) phosphonium sulfate (THPS), and dialdehydes.

Biocides can include hypochlorite bleach, hydrogen peroxide, peracetic acid, potassium monopersulfate, bromochlorodimethylhydantoin, dichloromethylethylhydantoin, chloroisocyanurate, tributyl tetradecyl phosphonium chloride (TTPC), dibromonitrilopropionamide, thiocyanomethylbenzyothiazole, methyldithiocarbamate, tetrahydrodimethylthiadiazonethione, tributyltin oxide, bromonitropropanediol, bromonitrostyrene, methylene bisthiocyanate, chloromethyl/methylisothiazolone, bensiosthiazolone, dodecylguanidine hydrochloride, polyhexamethylene biguanide, tetrakishydroxymethyl phosphonium sulfate, glutaraldehyde, alkyldimethylbenzyl ammonium chloride, didecyldimethylammonium chloride (DDAC), poly[oxyethylene (dimethyliminio) dichloride], decylthioethanamine, sodium dimethyldithiocarbamate, disodium ethylene bisdithiocarbamate, glutaraldehyde, terbuthylazine, isothiazolin; methylene bisthiocyanate; glutaraldehyde; DBNPA; carbamate; quaternary ammonium compounds; 4,5-dichloro 1,2-dithio-3-one; 4,5-dichloro-2-N-octyl-4-isothiazolin-3-one, 2-(p-hydroxyphenol) glyoxylohydroximoyl chloride, 2-(thiocyanomethylthio)benzothiazole ("TCMTB"); isothiazolone biocide, 3-5-Dimethyl-tetrahydro-2H-1,3,5-thiadiazine-2-thione, Methylene bisthiocyanate, 1-Alkyl(C16-18)amino-3-aminopropane acetate & Bis(trichloromethyl) sulfone, 5-Chloro-2-methyl-4-isothiazolin-3-one & 2-Methyl-4-isothiazolin-3-one, Alkyl dimethylbenzylammonium chloride & Dialkyl methyl benzylammonium chloride, 2,2-Dibromo-3-nitrilopropionamide (DBNPA), 2-(Thiocyanomethylthio)-benzothiazole & Bis(trichloromethyl) sulfone, Sodium dimethyldithiocarbamate & Disodium ethylene bis-dithiocarbamate, Glutaraldehyde(1,5pentanediol), 1-(3-Chloroallyl)-3,5,7-triazoniaadamatane chloride, N-4-Dihydroxy-alpha-oxobenzene chloride, Sodium hypochlorite, 4,5-dichloro-1,2-dithio-3-one, Decylthioethylamine, and Dodecylquandine hydrochloride.

The biocide can be administered to a medium to control microorganisms at a concentration of at least about 5 ppm, at least about 10 ppm, at least about 20 ppm, at least about 30 ppm, at least about 40 ppm, at least about 50 ppm, at least about 60 ppm, at least about 70 ppm, at least about 75 ppm, at least about 80 ppm, at least about 90 ppm, at least about 100 ppm, at least about 120 ppm, at least about 140 ppm, at least about 150 ppm, at least about 160 ppm, at least about 180 ppm, at least about 200 ppm, at least about 225 ppm, at least about 250 ppm, at least about 275 ppm, at least about 300 ppm, at least about 400 ppm, at least about 500 ppm, at least about 600 ppm, at least about 700 ppm, at least about 800 ppm, at least about 900 ppm, at least about 1000 ppm, at least about 1100 ppm, at least about 1200 ppm, at least about 1300 ppm, at least about 1400 ppm, at least about 1500 ppm, at least about 1600 ppm, at least about 1700 ppm, at least about 1800 ppm, at least about 1900 ppm, at least about 2000 ppm, at least about 2100 ppm, at least about 2200 ppm, at least about 2300 ppm, at least about 2400 ppm, at least about 2500 ppm, at least about 2600 ppm, at least about 2700 ppm, at least about 2800 ppm, at least about 2900 ppm, at least about 3000 ppm, at least about 3100 ppm, at least about 3200 ppm, at least about 3300 ppm, at least about 3400 ppm, at least about 3500 ppm, at least about 3600 ppm, at least about 3700 ppm, at least about 3800 ppm, at least about 3900 ppm, at least about 4000 ppm, at least about 4100 ppm, at least about 4200 ppm, at least about 4300 ppm, at least about 4400 ppm, at least about 4500 ppm, at least about 4600 ppm, at least about 4700 ppm, at least about 4800 ppm, at least about 4900 ppm, at least about 5000 ppm, at least about 5100 ppm, at least about 5200 ppm, at least about 5300 ppm, at least about 5400 ppm, at least about 5500 ppm, at least about 5600 ppm, at least about 5700 ppm, at least about 5800 ppm, at least about 5900 ppm, at least about 6000 ppm, at least about 6100 ppm, at least about 6200 ppm, at least about 6300 ppm, at least about 6400 ppm, at least about 6500 ppm, at least about 6600 ppm, at least about 6700 ppm, at least about 6800 ppm, at least about 6900 ppm, at least about 7000 ppm, at least about 7100 ppm, at least about 7200 ppm, at least about 7300 ppm, at least about 7400 ppm, at least about 7500 ppm, at least about 7600 ppm, at least about 7700 ppm, at least about 7800 ppm, at least about 7900 ppm, at least about 8000 ppm, at least about 8100 ppm, at least about 8200 ppm, at least about 8300 ppm, at least about 8400 ppm, at least about 8500 ppm, at least about 8600 ppm, at least about 8700 ppm, at least about 8800 ppm, at least about 8900 ppm, at least about 9000 ppm, at least about 9100 ppm, at least about 9200 ppm, at least about 9300 ppm, at least about 9400 ppm, at least about 9500 ppm, at least about 9600 ppm, at least about 9700 ppm, at least about 9800 ppm, at least about 9900 ppm, or at least about 10,000 ppm.

The biocide can be present in a medium in an amount of 0.01 wt % to 10 wt %, 0.1 wt % to 8 wt %, 0.5 wt % to 7 wt %, 1 wt % to 6 wt %, 2 wt % to 5 wt %, or 3 wt % to 4 wt %, based on total weight of the medium. The biocide can be present in a medium in an amount of at least about 0.01 wt %, at least about 0.1 wt %, at least about 0.5 wt %, at least about 1.0 wt %, at least about 1.5 wt %, at least about 2.0 wt %, at least about 2.5 wt %, at least about 3.0 wt %, at least about 3.5 wt %, at least about 4.0 wt %, at least about 4.5 wt %, at least about 5.0 wt %, at least about 5.5 wt %, at least about 6.0 wt %, at least about 6.5 wt %, at least about 7.0 wt %, at least about 7.5 wt %, at least about 8.0 wt %, at least about 8.5 wt %, at least about 9.0 wt %, at least about 9.5 wt %, or at least about 10.0 wt %, based on the total weight of the medium.

4. MEDIUM

The method described above can be performed by sampling, analyzing and/or monitoring any medium that can be adapted for use in flow cytometry. The medium can include water, such as oceanic water, an industrial process water stream, such as diluted soil, an oil and gas fluid, a food and beverage fluid, a medical fluid, or a combination thereof.

Industrial process water stream can include flume water, shower water, washers, thermal processing waters, brewing liquids, fermentation liquids, CIP (clean in place) liquids, hard surface sanitization liquids, ethanol/bio-fuels process waters, pretreatment and utility waters, water distribution systems, cooling towers, boiler systems, aquaria, sprinklers, spas, cleaning bath systems, air washers, pasteurizers, air conditioners, fluid transporting pipelines, storage tanks, ion exchange resins, membrane system liquids, ion-exchange bed liquids, water used in the process/manufacture of paper, such as pulping and papermaking suspensions, ceiling tiles, fiber board, or microelectronics, E-coat liquids, electrodeposition liquids, process cleaning liquids, oil exploration services liquids, oil well completion fluids, oil well workover fluids, oil field fluid samples, field fluid samples, drilling additive fluids, oil fracturing fluids, oil and gas wells, flowline water systems, natural gas water systems, food and beverage processing lines, beverage dispensing lines, paint spray booths, metalworking fluid baths, coal and mineral slurries, metal leaching fluids, wastewater treatment facilities, mollusk control, acid mine drainage, oil drilling pipes, oil pipelines, oil storage tanks, gas drilling pipes, gas pipelines, or any industrial application prone to microbial induced bio-film formation or microbial induced corrosion, and any combination thereof. The medium can be stimulated field fluid, oilfield water or lysogeny broth (LB) medium.

A medical fluid can include a sample of blood, tissue, urine, serum, plasma, amniotic fluid, cerebrospinal fluid, placental cells or tissue, endothelial cells, leukocytes, or monocytes. Any cell type, tissue, or bodily fluid can be utilized to obtain a sample. Such cell types, tissues, and fluid can include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues can also include lymph fluid, ascetic fluid, gynecological fluid, urine, peritoneal fluid, cerebrospinal fluid, a fluid collected by vaginal rinsing, or a fluid collected by vaginal flushing. A tissue or cell type can be provided by removing a sample of cells from an animal, but can also be accomplished by using previously isolated cells (e.g., isolated by another person, at another time, and/or for another purpose). Archival tissues, such as those having treatment or outcome history, can also be used. Protein or nucleotide isolation and/or purification may not be necessary.

5. MICROORGANISMS MEASURED

The medium sampled, analyzed and/or monitored for the method described above contains at least one microorganism and the biocides performance is measured by its' ability to control the microorganism. The microorganism can be prokaryotic, eukaryotic or both. The microorganism can be archaebacteria, aerobic bacteria, anaerobic bacteria, facultative anaerobic bacteria, hydrocarbon oxidizing organisms, iron bacteria, sessile bacteria, strict anaerobe, plankton, zooplankton, phytoplankton, biofilm bacteria, surface attached (sessile) bacteria, algae, protozoa, fungi, copepods, planktonic bacteria, thermophilic bacteria, sulfur-oxidizing bacteria, sulfate-reducing bacteria, iron bacteria. The microorganism can be any organism that can be found in water, such as oceanic or salt water or fresh water, oil and gas fluid, a food and beverage fluid, a medical fluid, or a combination thereof.

Bacterial species include *Achromobacter, Acidovorax, Acinetobacter johnsonii, Aeromonas hydrophila, Agrobacterium, Alcaligenes faecalis*, Alteromonadaceae (such as *Pelagibacter*), Bacillaceae *bacterium*, such as *Bacillus acidogenesis, Bacillus cereu, Bacillus macrolides, Bacillus megaterium, Bacillus sphaericus, Brachybacterium* species, such as *Brachybacterium paraconglomeratum, Brevibacterium* species, such as *Brevibacterium casei, Brevundimonas* species, such as *Brevundimonas diminuta, Burkholderia* species, such as *Burkhokderia vienamiensis, Burkholderia cepacia*, Burkholderiaceae (such as *Burkholderia* and *Comamonas*), *Campylobacter jejuni, Cellulomonas cellasea, Cellulomonas gelida, Clostridium* species, such as *Clostridium botulinum* and *Clostridium perfringens*, Comamonadaceae, *Cytophaga arvensicola, Deinococcus grandis, Delftia* species, such as *Delftia acidovorans, Dietzia* species, *Escherichia coli*, Enterobacteriaceae, *Flavobacterium spiritivorum, Gluconacetobacter, Halobacterium salinarum, Hippea* species, such as *Hippea maritime, Leptotrichia* species, *Listeria monocytogenes, Marinobacter, Methanocalculus pumilus, Methanocaldococcus interns, Methanoculleus thermophilitcus, Methanomethylovorans victoriae, Methanosarcina barkeri, Methanosarcina mazei, Methanothermobacter thermautotrophicus, Methanothrix soehngenii, Methylobaceterium* species, such as *Methylobaceterium rhodinum*, Moraxellaceae, *Ochrobactrum* species, such as *Ochrobactrum anthropi, Ochrobactrum grignonense*, and *Ochrobactrum tritici*, Oxalobacteraceae, *Peptostreptococcus* species, *Polphyromonas* species, *Propionibacterium acnes*, Pseudomonadaceae, such as *Pseudomonas aeruginosa* and *Pseudomonas putida, Pyrodictium occultum, Salmonella*, a bacteria from SAR11 clade, a lineage of bacteria from the Alphaproteobacteria class, *Shigella* species, *Slenotrophomonas maltophilia, Staphylococcus* species, such as *Staphylococcus aureus* and *Staphylococcus lentus, Stenotrophomonas* species, such as *Stenotrophomonas maltophilia, Streptococcus* A, *Tissierella* species, Veillonellaceae species, such as *Pelosinus, Vibrio* species, such as *Vibrio cholerae, Vibrio parahaemolyticus*, and *Vibrio vulnificus*, and Xanthomonadaceae.

6. FLOW CYTOMETRY

The method described above utilizes flow cytometry. As used herein, flow cytometry can broadly be described as a method that provides a flowing stream of particles and individually interrogates those particles spectroscopically.

To provide the stream of particles, flow cytometry generally employs the principle of hydrodynamic focusing. Hydrodynamic focusing provides a stream of particles which pass through an active region, typically located within a flow cell, in which the particles are exposed to radiation and at which a multitude of detectors are oriented to detect any radiation that emerges from the active region, via scatter, fluorescence, or any other mechanism.

Once the stream of particles is established, individual particles are subjected to spectroscopic interrogation. Electromagnetic radiation interacts with each particle that passes through the active region. One of skill in the art should appreciate that any spectroscopic interrogation is suitable for use with this invention, so long as it is capable of providing relevant information about the particle of interest. Flow cytometry measures forward scattering data, side scattering data, and fluorescence data. The flow cytometer is capable of independently exciting and independently detecting at least two distinct chromophores. Data can be measured using one or more excitation wavelength. The fluorescence emission wavelength can be 200 nm to 900 nm, 505 nm to 545 nm or 650 nm to 670 nm.

Examples of a flow cytometer suitable for use with the methods disclosed herein are the Gallios™ series flow cytometers, available commercially from Beckman Coulter, Inc., Pasadena, Calif. One particularly suitable example is the Gallios™ flow cytometer with 10 colors and 3 lasers (561 ready).

a. Preparation of Flow Cytometry Samples

The fluid samples from the medium can be collected by preparing a clean and preferably sterile container for sample collection. The container can be filled completely to leave no head space for air. The container can be taken to a clean lab space, its contents can be poured into a separation funnel, and the aqueous phase can be decanted into a sterile container.

A stock staining solution can be prepared using at least one selectivity agent. For example, a stock staining solution can be prepared using Sytox® Red Stain (S34859, available commercially from Life Technologies, Carlsbad, Calif.) and bis-(1,3-dibutyl barbituric acid)trimethin oxonol ($DiBAC_4(3)$) (B-438, available commercially from Life Technologies, Carlsbad, Calif.). The staining solutions can be made the day that the experiment is performed.

To test for biocide efficacy, the fluid samples can be mixed with an amount of interest of a biocide of interest, shaken from 50 to 100 times (consistent amount of shaking when comparing biocides to one another), and incubated at 37° C. for an amount of time of interest.

The field fluid with or without biocide can be mixed with a buffer, such as double filtered phosphate-buffered saline (dfPBS) and centrifuged. The supernatant can be poured off, the pellet can be gently broken apart, and dfPBS can be added and vortexed to provide a washed sample.

In order to quantify the particles of interest, a known concentration of inert particles of size and structure different than the particles of interest can be added to the medium to produce a stock counting bead solution. The stock counting bead solution can help establish a baseline for a comparison of concentration with the particles of interest. A stock counting bead, such as B-7277, available commercially from Life Technologies, Carlsbad, Calif., can be used in a stock counting bead solution.

A stock counting bead solution can be prepared by placing an aqueous suspension of 6 μm counting beads containing $1.0 \times 10^8$ beads/mL in a warm water bath for 10 minutes. The suspension can be vortexed for 15 seconds, then 200 μL of the suspension can be added to 4000 μL of dfPBS and can be vortexed for 40 seconds to produce a working counting bead stock.

To prepare a flow cytometry sample, a known amount of the stock counting bead solution can be mixed with a known amount of the stock staining solution under protection from light and vortexed for 5 seconds. Under protection from light, the washed sample can be added to this mixture, vortexed and incubated at room temperature. Flow cytometry samples not used immediately after this incubation can be stored at 4° C. for no longer than 30 minutes. Flow cytometry samples can generally not be used if more than 30 minutes has lapsed after preparation.

To compensate for background signals from dfPBS and counting beads, a neat dfPBS sample and the stock counting bead solution can be used.

b. Iron Chelators

The method described above can include contacting the sample with at least one iron chelator. The iron chelator can be added to the sample to chelate with the iron-containing suspended solids. This chelation of the iron-containing suspended solids aids in the quantification of the microbes since the chelation reduces the interference in the forward and side scatter contour density plots caused by the suspended iron-containing compounds. As can be seen in comparison of FIGS. 21A and 21B, the forward and side scatter contour density plots for FIG. 21B has many fewer particles detected in the upper right part of the plot as compared to the untreated contour plot of FIG. 21A.

Chelators are small molecules that bind very tightly to metal ions. Some chelators are simple molecules that are easily manufactured (e.g., ethylenediaminetetraacetic acid; EDTA). Others are complex proteins made by living organisms (e.g., transferrin). The key property shared by all chelators is that the metal ion bound to the chelator is chemically inert. Consequently, one of the important roles of chelators is to detoxify metal ions and prevent poisoning. For instance, EDTA is used to treat patients with extreme, life-threatening hypercalcemia. The iron chelator, desferrioxamine (Desferal®), is used to remove excess iron that accumulates with chronic blood transfusions. Many chelators are used in chemistry and industry. Only a few are clinically useful since most have dangerous side-effects. One important property required of clinically useful chelators is specificity. Since these drugs disperse diffusely in the body, they must bind the target metal ion preferentially over others. Desferrioxamine, for instance, can be used to treat iron overload since the drug binds iron with a large preference over other metal ions such as calcium ($Kd=10^{-31}M$ for iron, $Kd=10^{-9}M$ for calcium).

Iron chelators suitable for flow cytometry include citric acid, ascorbic acid, desferrioxamine, EDTA, lactoferrin, transferrin, polyacrylic acid, poly(acrylic acid: 2-acrylamido-2-methyl propane sulfonic acid: sulfonated styrene) (Poly-G), sodium hexametaphosphate, gluconic acid, tartaric acid, oxalic acid, an organic acid, a phosphonic acid, sodium thiosulfate, or a combination thereof.

c. Spectral Data

Spectral data can be used to define one or more subsets of microorganisms. Spectral data (spectroscopic signals) can be triggered and isolated by methods known to those of skill in the art. The spectral data can include forward scattering data, side scattering data, fluorescence data, or a combination thereof. The forward scattering data, the side scattering data, or both can be utilized to provide a gate to isolate data related to particles of interest. Typically, forward scattering data corresponds to the size of a particle and side scatter data corresponds to the structure of a particle.

The data can be presented in a bivariate density plot of the forward scattering data versus the side scattering data, which provides the ability to distinguish between particles having the same size, but different structures, or between particles having the same structure, but different size. As an example of utilizing a gate in this fashion, one can select a sub-set of particles having forward scattering data and side scattering data that fall within a certain range, thus correlating to particles of a certain size and structure, and observe fluorescence data from just the sub-set of particles. For example, the plot can show visualizations of the respective gates of all particles, the counting beads, all bacteria, budding bacteria, and stationary bacteria.

The data can be presented in a bivariate density plot of the fluorescence signal from a first wavelength range versus the fluorescence signal from a second wavelength range, for example, the fluorescence signal from 650 nm to 670 nm versus the fluorescence signal from 505 nm to 545 nm. The plot can show visualizations of the respective gates for viable cells, membrane-damaged cells, depolarizing and/or depolarized cells, and membrane-damaged and depolarized cells, which are each subsets of the overall microorganism. For example, higher fluorescence intensity along the y-axis can correlate to more membrane damage and higher fluorescence intensity along the x-axis can correlate to greater depolarization.

The data can be presented as a bar graph visually representing the fluorescence data for the sample. Each bar can represent the number of bacterial cells corresponding to the fluorescence data for each respective sample. The number of bacterial cells in each subset, i.e., viable cells, depolarized cells, membrane-damaged cells and membrane-damaged and depolarized cells, in the sample can be correlated to the number of hits that occurs within the respective gate.

7. SELECTIVITY AGENT

The method described above can include contacting the microorganism with at least one selectivity agent to produce a labeled microorganism. The selectivity agent can include a label that can be used with a flow cytometer. The label can be a fluorophore, a cell viability label, a quantum dot, an isotope label, such as lanthanide isotopes, or a combination thereof. A selectivity agent can be a fluorophore and a cell viability label.

a. Fluorophores

The selectivity agent can include a fluorophore, also known as "fluorescent labels" and "fluors," that can be attached to an antibody that recognizes a target feature on or in the cell or can be attached to a chemical entity with affinity for the cell membrane or another cellular structure. A fluorophore has a characteristic peak excitation and emission wavelength and can be used in combination with another fluorophore having a different characteristic peak excitation and emission wavelength, wherein the emission spectra can overlap. The fluorophore can include a rhodamine, rhodamine B, N,N,N',N' tetramethyl-6-carboxyrhodamine (TAMRA), 6-carboxy-X-rhodamine (ROX), 6-carboxyrhodamine (R6G), Rhodamine Green, Rhodamine Red, 4,7-dichlorotetramethyl rhodamine (DTAMRA), lissaminerhodamine B sulfonyl chloride rhodamine (Rhod), rhodamine 123, rhodamine X, Alexa dyes (e.g., Alexa Fluor-350, -430, -488, -532, -546, -568, -594, -663 and -660), DyLight 594, isothiocyanate, sulforhodamine B, sulforhodamine 101, sulfonyl chloride derivative of sulforhodamine 101 (Texas Red); tetramethyl rhodamine; tetramethyl rhodamine isothiocyanate (TRITC), fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2,'7'-dimethoxyfluorescein (JOE),6-JOE, 5-carboxy-2',4',5',7'-tetrachlorofluorescein (ZOE) rhodol, fluorescein isothiocyanate, cyanine dyes, including Cy2, Cy 3, Cy3B, Cy 3.5, Cy 5, Cy 5.5, Cy 7 and Cy 7.5, carbocyanine, dicarbocyanine, merocyanine, coumarin, 7-amino-4-methylcoumarin, aminocoumarin, hydroxycoumarin, 4-dicyanomethylene-2-methyl-6-(p(dimethylamino)styryl)-4H-pyran (DCM), pyrromethene, stilbene, umbelliferone, tetracene, malachite green, macrocyclic chelates of lanthanide ions (e.g., quantum dye, etc.), AMCA, BODIPY 630/650, BODIPY 650/665, BODIPY-FL, BODIPY-R6G, BODIPY-TMR, BODIPY-TRX, Oregon Green 488, Oregon Green 500, Oregon Green 514, Pacific Blue, PicoGreen, eosins and erythrosins, phycocyanin, allophycocyanin, o-phthaldehyde, fluorescent nonparticles (e.g. Q dots) and fluorescamine, 8-anilino-1-napthalene sulfonate, Cascade blue, Cascade Yellow, Marina Blue, dimethylaminonaph-thalene sulfonic acid (dansyl), pyrene, anthracene, nitrobenz-oxadiazole (NBD), Auramine O, acridine and dipyrrometheneboron difluoride, Acridine Orange, Acridine Yellow, an Atto dye, coelenterazine, 4',6-diamidino-2-phenylindole (DAPI), FLUO 3, FURA 2,5-hydroxytryptamine (HAT), a Hoechst dye, INDO 1, JC-1 dye, Lucifer Yellow, Nile Red, propidium iodide, QUIN 2, or seminaphtharhodafluor (SNARF).

b. Cell Viability Labels

The selectivity agent can be a cell viability label. The cell viability label can include traditional or impermeant nucleic acid dyes, such as 4',6-Diamidino-2-phenylindole, dihydrochloride (DAPI), SYTOX® Blue Dead Cell Stain, SYTOX® Green Nucleic Acid Stain, Propidium iodide, Ethidium homodimer-1 (EthD-1), Ethidium homodimer-2 (EthD-2), Ethidium monoazide bromide (EMA), 7-Aminoactinomycin D (7-AAD), SYTOX® AADvanced™ Dead Cell Stain Kit, SYTOX® Red Dead Cell Stain, SYTOX® Blue Dead Cell Stain, for flow cytometry, SYTOX® Blue Nucleic Acid Cell Stain, SYTOX® Green Dead Cell Stain, for flow cytometry, SYTOX® Green Nucleic Acid Stain, SYTOX® Orange Dead Cell Stain, for flow cytometry, SYTOX® Orange Nucleic Acid Stain, SYTOX® Red Dead Cell Stain, SYTOX® AADvanced™ Dead Cell Stain, and SYTOX® Dead Cell Stain Sampler Kit, monomeric cyanine dyes, such as PO-PRO™-1 iodide (435/455), YO-PRO®-1 iodide (491/509), and TO-PRO®-3 iodide (642/661), dimeric cyanine dyes, such as POPO™-1 iodide (434/456), YOYO®-1 iodide (491/509), and TOTO®-1 iodide (514/533), amine-reactive dyes, such as LIVE/DEAD® Fixable Blue Dead Cell Stain Kit, LIVE/DEAD® Fixable Violet Dead Cell Stain Kit, LIVE/DEAD® Fixable Aqua Dead Cell Stain Kit, LIVE/DEAD® Fixable Yellow Dead Cell Stain Kit, LIVE/DEAD® Fixable Green Dead Cell Stain Kit, LIVE/DEAD® Fixable Red Dead Cell Stain Kit, LIVE/DEAD® Fixable Far Red Dead Cell Stain Kit, and LIVE/DEAD® Fixable Near-IR Dead Cell Stain Kit, Annexin V conjugates, such as Annexin V, Pacific Blue™ Conjugate, Annexin V, R-phycoerythrin Conjugate (R-PE annexin V), and Annexin V, Alexa Fluor® 647 Conjugate, and membrane potential probes, such as Bis Oxonol, such as Bis-(1,3-Dibutylbarbituric Acid)Trimethine Oxonol (DiBAC4(3)), BacLight™ Bacterial Membrane Potential Kit—for Flow Cytometry, Bis-(1,3-Dibutylbarbituric Acid) Trimethine Oxonol (DiBAC4(3)), FluoroPure™ grade, Bis-(1,3-Dibutylbarbituric Acid)Pentamethine Oxonol (DiBAC4(5)), Bis-(1,3-Dibutylbarbituric Acid)Trimethine Oxonol (DiBAC4(3)), Bis-(1,3-Diethylthiobarbituric Acid)Trimethine Oxonol (DiSBAC2(3)), CC2-DMPE, CC2-DMPE, DiS- BAC2(3), DiSBAC2(3), DiSBAC4(3), DiSBAC4(3), Oxonol V (bis-(3-Phenyl-5-Oxoisoxazol-4-yl)Pentamethine Oxonol), 3,3'-Diethyloxadicarbocyanine Iodide, 3,3'-Dihexyloxacarbocyanine Iodide, 5-Carboxyfluorescein Diacetate, Calcein-AM, SynaptoGreen™ Reagent, SynaptoRed™ Reagent, Thiol Fluorescent Probe IV, and Zinbo-5.

8. FIELDS OF USE

The method describe above can be used in any field that uses biocides to control microorganisms including, but not limited to, fields of molecular biology, pathology, immunology, plant biology and marine biology. The methods can be used in various industries such as Pulp & Paper, Healthcare, Food & Beverage, Upstream Oil & Gas Systems, Downstream Oil & Gas Systems, Industrial Water (Cooling and Process Water), Oilfield Process Water, Oilfield and refinery produced water, and Institutional.

9. EXAMPLES

The foregoing can be better understood by reference to the following examples, which are presented for purposes of illustration and are not intended to limit the scope of the invention.

Example 1

Preparation of Flow Cytometry Samples

Field fluid samples were collected by preparing a clean and preferably sterile container for sample collection. The container was filled completely to leave no head space for air. The container was taken to a clean lab space, its contents were poured into a separation funnel, and the aqueous phase was decanted into a sterile container.

A stock counting bead solution was prepared by placing an aqueous suspension of 6 μm counting beads containing $1.0 \times 10^8$ beads/mL (B-7277, available commercially from Life Technologies, Carlsbad, Calif.) in a warm water bath for 10 minutes. The suspension was vortexed for 15 seconds, then 200 μL of the suspension was added to 4000 μL of dfPBS and vortexed for 30 seconds to produce a stock counting bead solution. The concentration of the stock counting bead solution was measured using a hemocytometer and standard methods.

A stock staining solution was prepared by mixing 50 μL of Sytox® Red Stain (S34859, available commercially from Life Technologies, Carlsbad, Calif.) and 100 μL of a 0.5 mg/mL solution of bis-(1,3-dibutyl barbituric acid)trimethin oxonol ($DiBAC_4(3)$) (B-438, available commercially from Life Technologies, Carlsbad, Calif.) and vortexing the resulting solution for 30 seconds, pulse centrifuging the solution for 10 seconds, vortexing for 15 seconds and pulse centrifuging for 5 seconds. The resulting solution was stored in an opaque container and protected from light. New staining solutions were made every day that experiments were performed.

If biocide efficacy was to be tested, about 100 mL of field fluid sample was mixed with an amount of interest of a biocide of interest, shaken from 50 to 100 times (consistent amount of shaking when comparing biocides to one another), and incubated at 37° C. for an amount of time of interest.

About 500 μL of field fluid with or without biocide was mixed with 900 μL of dfPBS and centrifuged at 10,000×g. The supernatant was poured off, the pellet was gently broken apart, and dfPBS was added to a final volume of 400 μL and vortexed for 5 seconds to provide a washed sample.

When iron chelators were used to reduce signal interference, about 500 μL of field fluid sample was mixed with 1500 μL of dfPBS and vortexed for 5 seconds. The resulting solution was centrifuged at 10,000×g for 4 minutes, and the supernatant was removed by aspirating or decanting without disturbing the pellet. The pellet was gently broken apart, and 1980 μL of dfPBS and 20 μL of 1M citric acid (final concentration of 10 mM) were added to the pellet. The resulting solution was vortexed for 10 seconds and allowed to sit for about 30 additional seconds. The solution was then centrifuged at 10,000×g for 4 minutes, and the supernatant was again removed by aspirating or decanting without disturbing the pellet. The pellet was gently broken apart, and 400 μL of dfPBS was added to the pellet and vortexed for 5 seconds. The sample was then added to a prepared flow tube.

To prepare a flow cytometry sample, a known amount of the stock counting bead solution was mixed with a known amount of the stock staining solution under protection from light and vortexed for 5 seconds. Under protection from light, 400 μL of the washed sample was added to this mixture, vortexed for 5 seconds and incubated for 5 minutes at room temperature. If flow cytometry samples were not intended to be used immediately after this incubation, then samples were stored at 4° C. for no longer than 30 minutes. Flow cytometry samples were generally not used if more than 30 minutes had lapsed after preparation.

To compensate for background signals from dfPBS and counting beads, a neat dfPBS sample and the stock counting bead solution were used.

Example 2

Biocide Efficacy

The efficacy of the biocide orthophythaldehyde+DDAC quaternary ammonium compound in a 1:2 wt.ratio at controlling *Escherichia coli* (*E. coli*) growth in LB media was evaluated. A simulated field fluid was prepared containing LB media without any biocide chemical treatment which was separated into batches to which 0 ppm, 75 ppm, 150 ppm, 300 ppm, 600 ppm, and 1200 ppm of the biocide were added, respectively. Half of the batch containing zero biocide ("UnTreated 0 hr") and the batches to which biocide was added were prepared into flow cytometry samples according to Example 1. The remaining half of the batch containing zero biocide was incubated for four hours ("UnTreated 4 hr") at 37° C. prior to being prepared into a flow cytometry sample according to the procedure set forth above.

Flow cytometry was performed on all flow cytometry samples using a Gallios™ flow cytometer with 10 colors and 3 lasers (561 ready), and data was collected for forward scattered signal, side scattered signal, fluorescence signal from 505 nm to 545 nm (corresponding to the fluorescence emission wavelength of $DiBAC_4(3)$) and fluorescence signal from 650 nm to 670 nm (corresponding to the fluorescence emission wavelength of Sytox® Red Stain).

Figure 3:
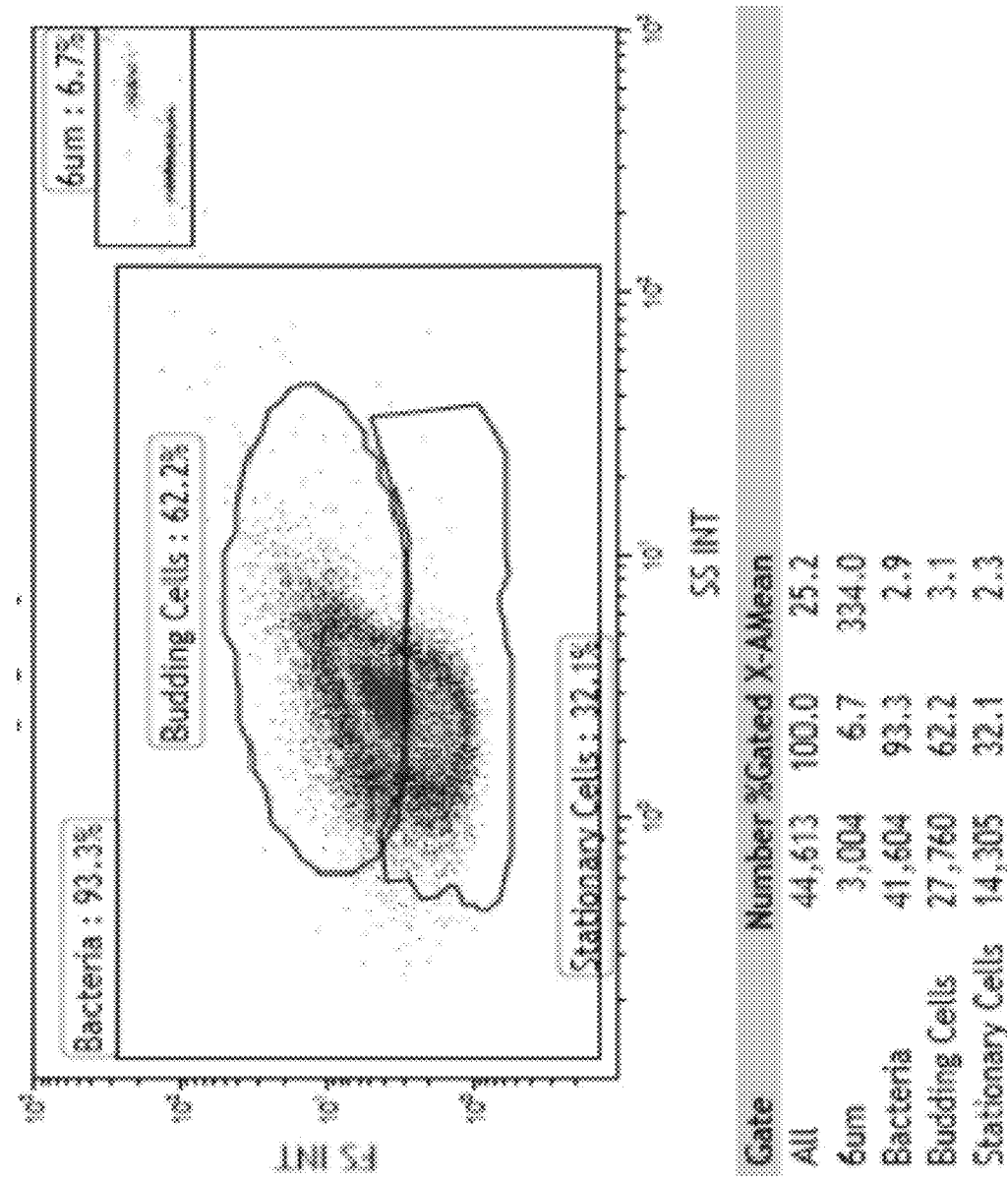
FIG. 3 depicts a plot of the forward scattered signal versus the side scattered signal.
Figure 4:
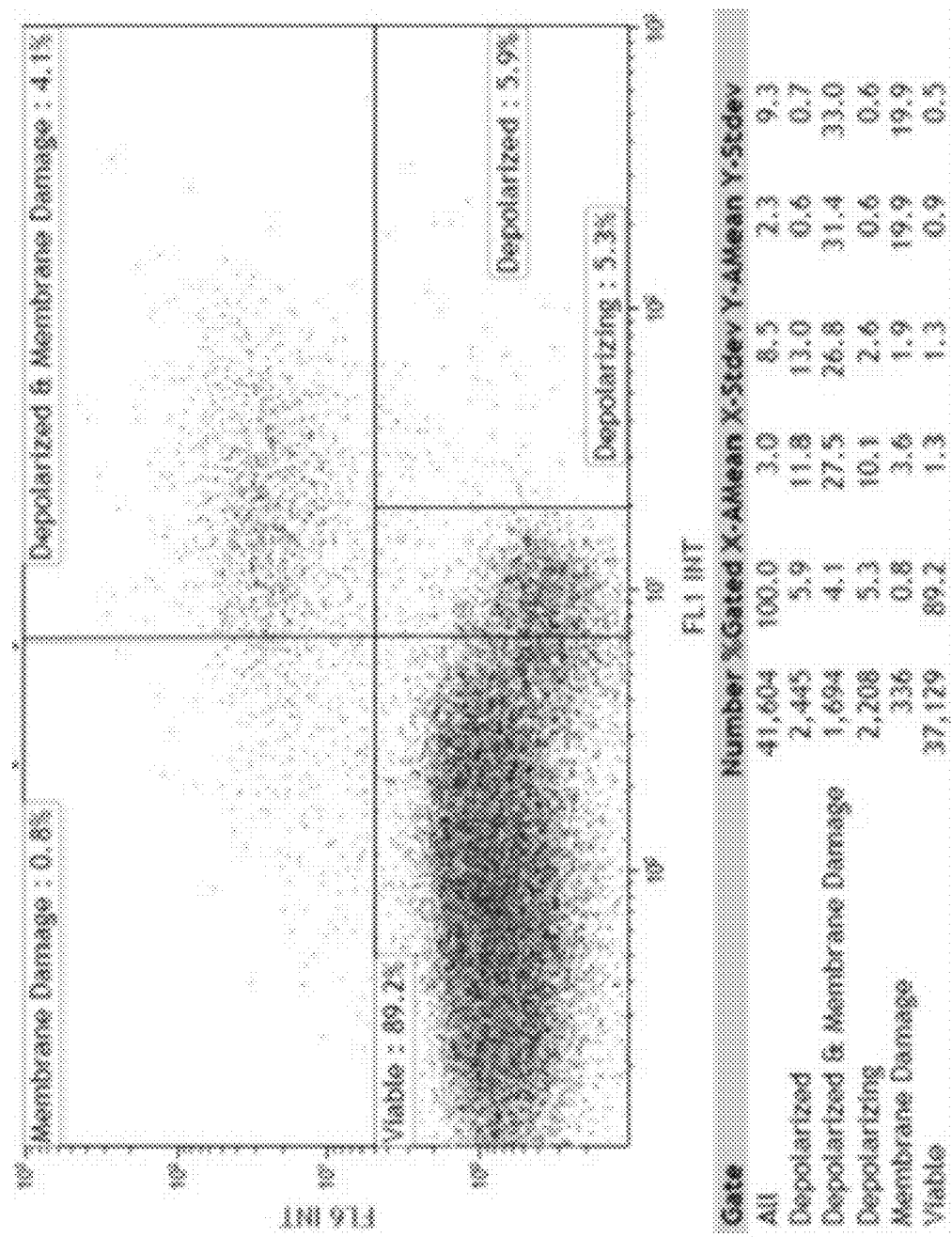
FIG. 4 depicts a plot of the fluorescence signal from 650 nm to 670 nm versus the fluorescence signal from 505 nm to 545 nm.

Data for the Untreated 0 hr sample are shown in FIGS. 3-4.

A plot of the forward scattered signal versus the side scattered signal is shown in FIG. 3 (top). The enclosed shapes within the plot are visualizations of the respective gates all particles (All), the counting beads (6 um), all bacteria (Bacteria), budding bacteria (Budding Cells) and stationary bacteria (Stationary Cells). The data is shown in FIG. 3 (bottom).

A plot of the fluorescence signal from 650 nm to 670 nm versus the fluorescence signal from 505 nm to 545 nm is shown in FIG. 4 (top). The rectangles within the plot are visualizations of the respective gates for viable cells, membrane-damaged cells, depolarizing cells, depolarized cells, and membrane-damaged and depolarized cells, which are each subsets of the overall bacteria. The data is shown in FIG. 4 (bottom).

Figure 5:
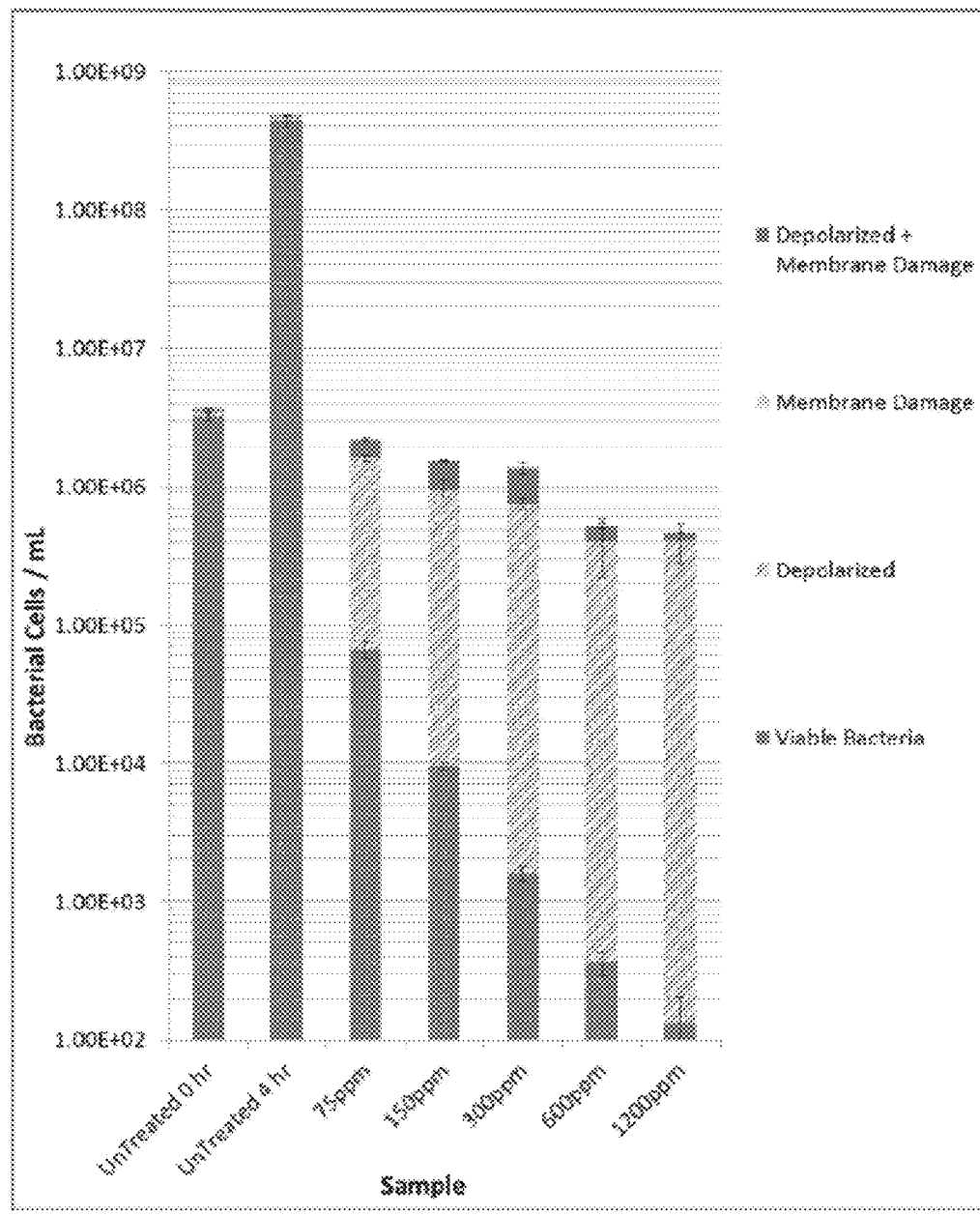
FIG. 5 depicts a bar graph visually representing the fluorescence data for each of the samples.

A bar graph visually representing the fluorescence data for each of the samples is shown in FIG. 5. The left-most bar represents the UnTreated 0 hr sample and is a visualization of the data of FIG. 4. Each of the other bars represents the number of bacterial cells corresponding to the fluorescence data for each respective sample. The number of bacterial cells in each subset is correlated to the number of hits that occurs within the respective gate. The data are shown in Table 1. Corresponding standard errors are shown in Table 2.

TABLE 1

|  | Viable/mL | Depolarized/mL | Membrane-damaged/mL | Depolarized and Membrane-damaged/mL |
|---|---|---|---|---|
| UnTreated 0 hr | 3.22E+06 | 2.45E+05 | 4.41E+04 | 1.65E+05 |
| UnTreated 4 hr | 4.43E+08 | 3.37E+07 | 3.02E+06 | 1.02E+07 |
| 75 ppm | 6.71E+04 | 1.56E+06 | 1.73E+03 | 5.56E+05 |
| 150 ppm | 9.45E+03 | 9.44E+05 | 1.66E+02 | 5.87E+05 |
| 300 ppm | 1.60E+03 | 7.48E+05 | 3.33E+01 | 6.26E+05 |
| 600 ppm | 3.65E+02 | 4.00E+05 | 0.00E+00 | 1.23E+05 |
| 1200 ppm | 1.32E+02 | 4.11E+05 | 3.32E+01 | 5.89E+04 |

TABLE 2

|  | Viable/mL | Depolarized/mL | Membrane-damaged/mL | Depolarized and Membrane-damaged/mL |
|---|---|---|---|---|
| UnTreated 0 hr | 2.28E+05 | 1.59E+04 | 1.57E+04 | 9.01E+03 |
| UnTreated 4 hr | 5.17E+07 | 4.09E+06 | 1.24E+06 | 2.76E+06 |
| 75 ppm | 9.31E+03 | 8.96E+04 | 4.57E+02 | 6.66E+04 |
| 150 ppm | 6.09E+02 | 1.54E+05 | 2.71E+01 | 5.79E+03 |
| 300 ppm | 1.89E+02 | 7.04E+04 | 2.72E+01 | 1.41E+05 |
| 600 ppm | 7.18E+01 | 1.82E+05 | 0.00E+00 | 1.49E+04 |
| 1200 ppm | 7.14E+01 | 1.27E+05 | 2.71E+01 | 1.83E+03 |

Example 3

Synergy Between Didecyldimethylammonium Chloride (DDAC) and Tributyl Tetradecyl Phosphonium Chloride (TTPC)

The synergy between the efficacy of biocides didecyldimethylammonium chloride (DDAC) and tributyl tetradecyl phosphonium chloride (TTPC) at controlling *E. coli* growth in LB media was evaluated. A simulated field fluid was prepared containing LB media without any biocide chemical treatment, which was separated into batches to which zero and 40 ppm of biocide in ratios (DDAC:TTPC) of 10:0, 9:1, 7:3, 5:5, 3:7, 1:9 and 0:10 were added, respectively. Half of the batch containing zero biocide ("UnTreated 0 hr") and the batches to which biocide was added were prepared into flow cytometry samples according to Example 1. The remaining half of the batch containing zero biocide was incubated for four hours ("UnTreated 4 hr") at 37° C. prior to being prepared into a flow cytometry sample according to Example 1.

Figure 6:
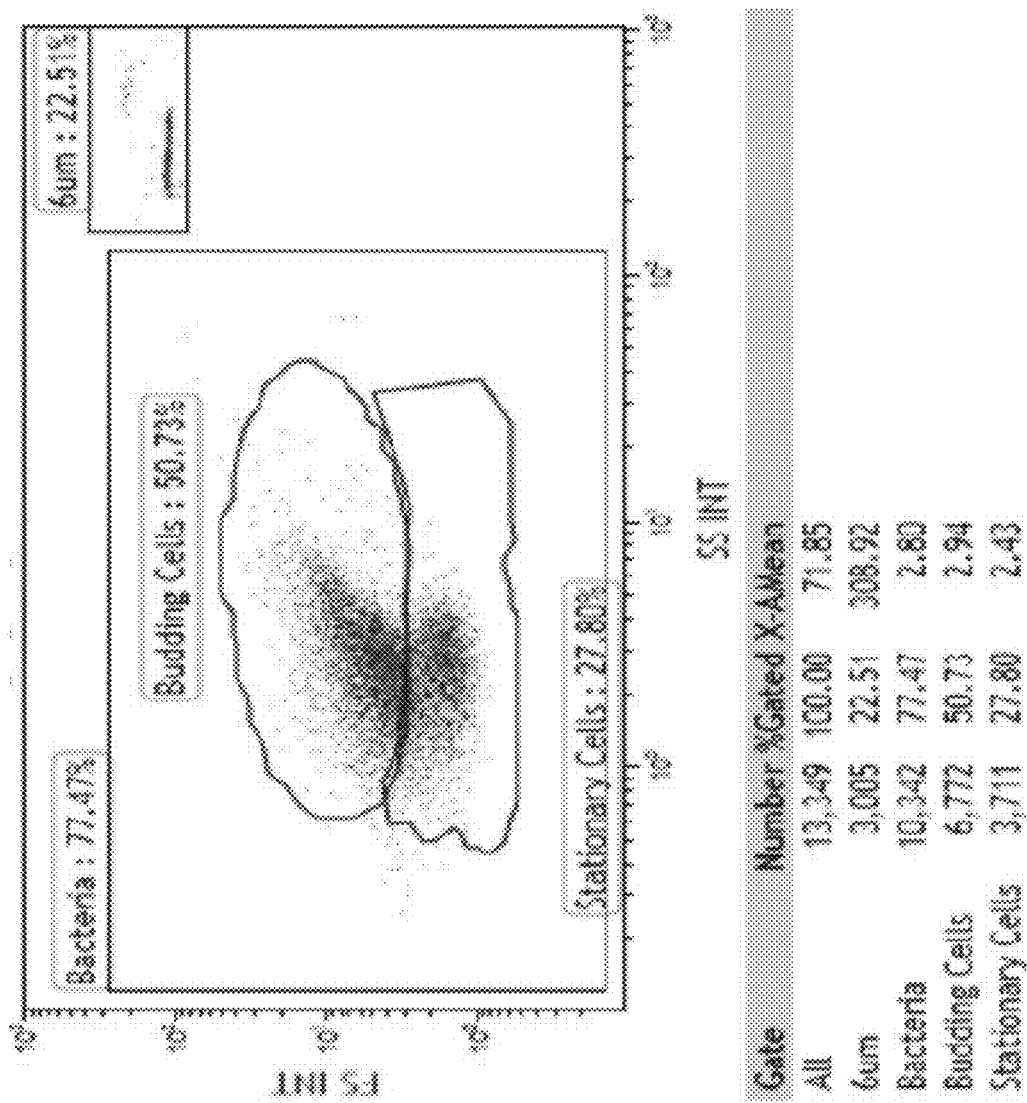
FIG. 6 depicts a plot of the forward scattered signal versus the side scattered signal.
Figure 7:
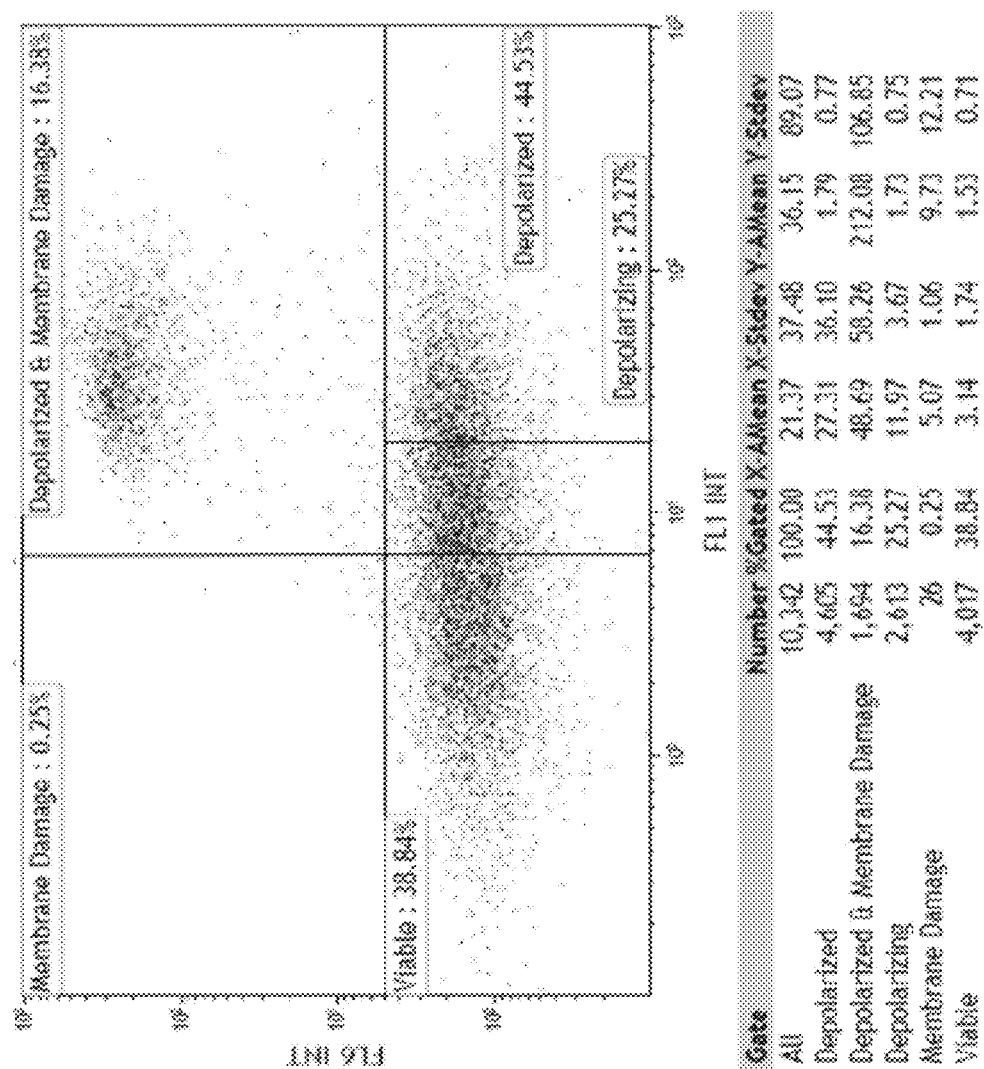
FIG. 7 depicts a plot of the fluorescence signal from 650 nm to 670 nm versus the fluorescence signal from 505 nm to 545 nm.
Figure 8:
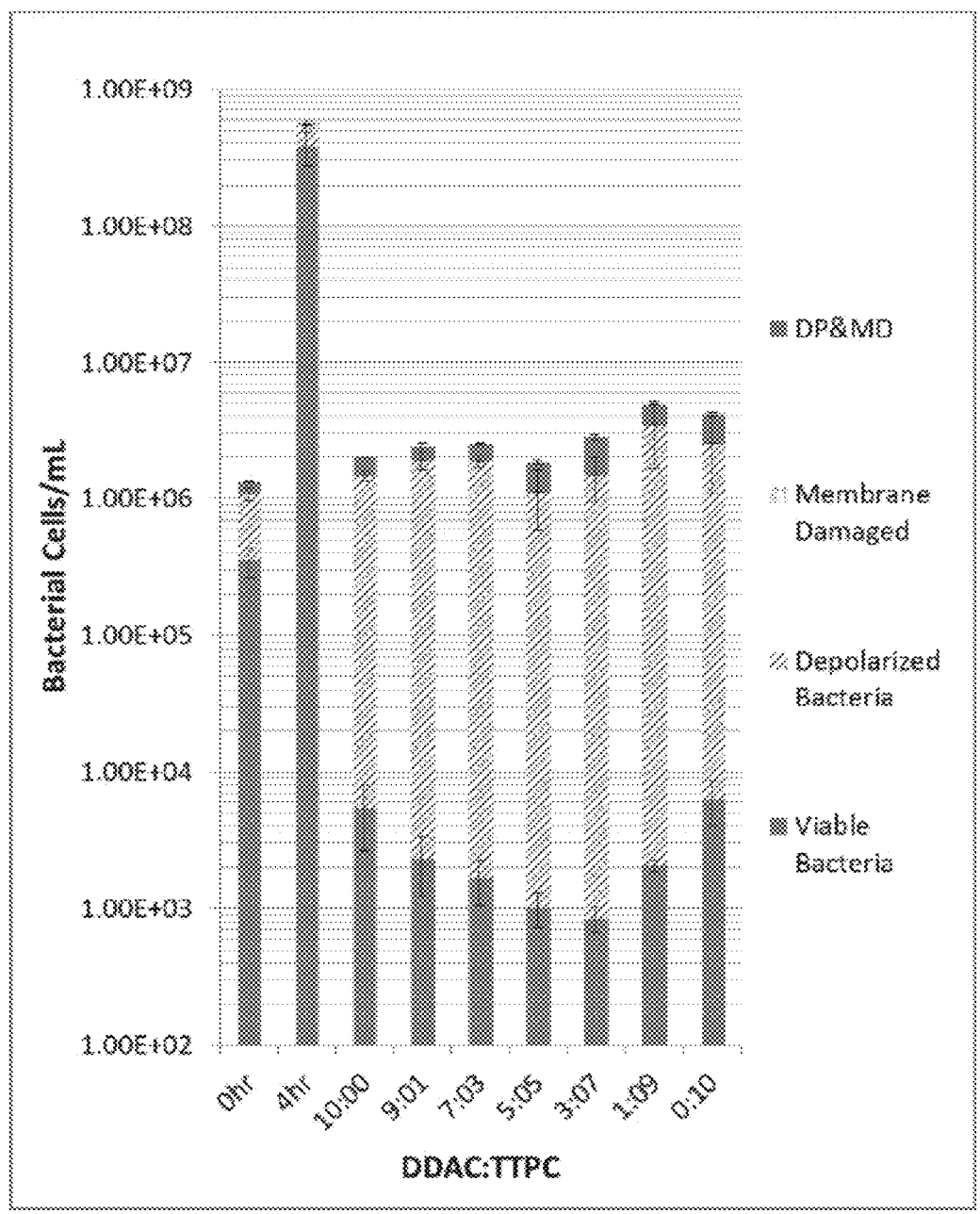
FIG. 8 depicts a bar graph visually representing the number of bacterial cells in the sub-sets of viable cells, depolarized cells, membrane-damaged cells and membrane-damaged and depolarized cells in a simulated field fluid after treatment with didecyldimethylammonium chloride and tributyl tetradecyl phosphonium chloride.

Flow cytometry was performed on all flow cytometry samples as set forth in Example 2. Data for the UnTreated 0 hr sample are shown in FIGS. 6-7 in the same fashion as described with respect to FIGS. 3-4 in Example 2. A bar graph visually representing the number of bacterial cells in the sub-sets of viable cells, depolarized cells, membrane-damaged cells and membrane-damaged and depolarized cells for each of the samples is shown in FIG. 8. The data are shown in Table 3 and corresponding standard errors are shown in Table 4.

TABLE 3

|  | Viable/mL | Depolarized/mL | Membrane-damaged/mL | Depolarized and Membrane-damaged/mL |
|---|---|---|---|---|
| UnTreated 0 hr | 3.52E+05 | 7.27E+05 | 3.00E+03 | 2.44E+05 |
| UnTreated 4 hr | 3.79E+08 | 1.58E+08 | 4.84E+06 | 2.15E+07 |
| 10:0 | 5.39E+03 | 1.45E+06 | 3.49E+02 | 5.55E+05 |
| 9:1 | 2.30E+03 | 1.91E+06 | 2.00E+02 | 4.76E+05 |
| 7:3 | 1.65E+03 | 1.87E+06 | 2.50E+02 | 6.55E+05 |
| 5:5 | 1.00E+03 | 1.11E+06 | 5.01E+01 | 7.44E+05 |
| 3:7 | 8.50E+02 | 1.48E+06 | 0.00E+00 | 1.34E+06 |
| 1:9 | 2.04E+03 | 3.42E+06 | 4.21E+02 | 1.48E+06 |
| 0:10 | 6.33E+03 | 2.54E+06 | 5.37E+02 | 1.67E+06 |

TABLE 4

|  | Viable/mL | Depolarized/mL | Membrane-damaged/mL | Depolarized and Membrane-damaged/mL |
|---|---|---|---|---|
| UnTreated 0 hr | 8.56E+04 | 1.10E+05 | 5.88E+02 | 3.08E+04 |
| UnTreated 4 hr | 1.04E+08 | 5.87E+07 | 2.36E+06 | 3.36E+06 |
| 10:0 | 2.75E+03 | 1.07E+05 | 1.76E+02 | 9.91E+03 |
| 9:1 | 1.06E+03 | 2.84E+05 | 1.41E+02 | 1.87E+05 |
| 7:3 | 6.00E+02 | 1.62E+05 | 3.55E+01 | 1.44E+04 |
| 5:5 | 2.83E+02 | 5.26E+05 | 3.54E+01 | 6.80E+04 |
| 3:7 | 1.76E+02 | 5.29E+05 | 0.00E+00 | 1.17E+05 |
| 1:9 | 1.84E+02 | 1.75E+06 | 2.27E+02 | 3.32E+04 |
| 0:10 | 2.36E+03 | 1.45E+06 | 1.67E+02 | 1.31E+05 |

Example 4

Oilfield Sample

Figure 9:
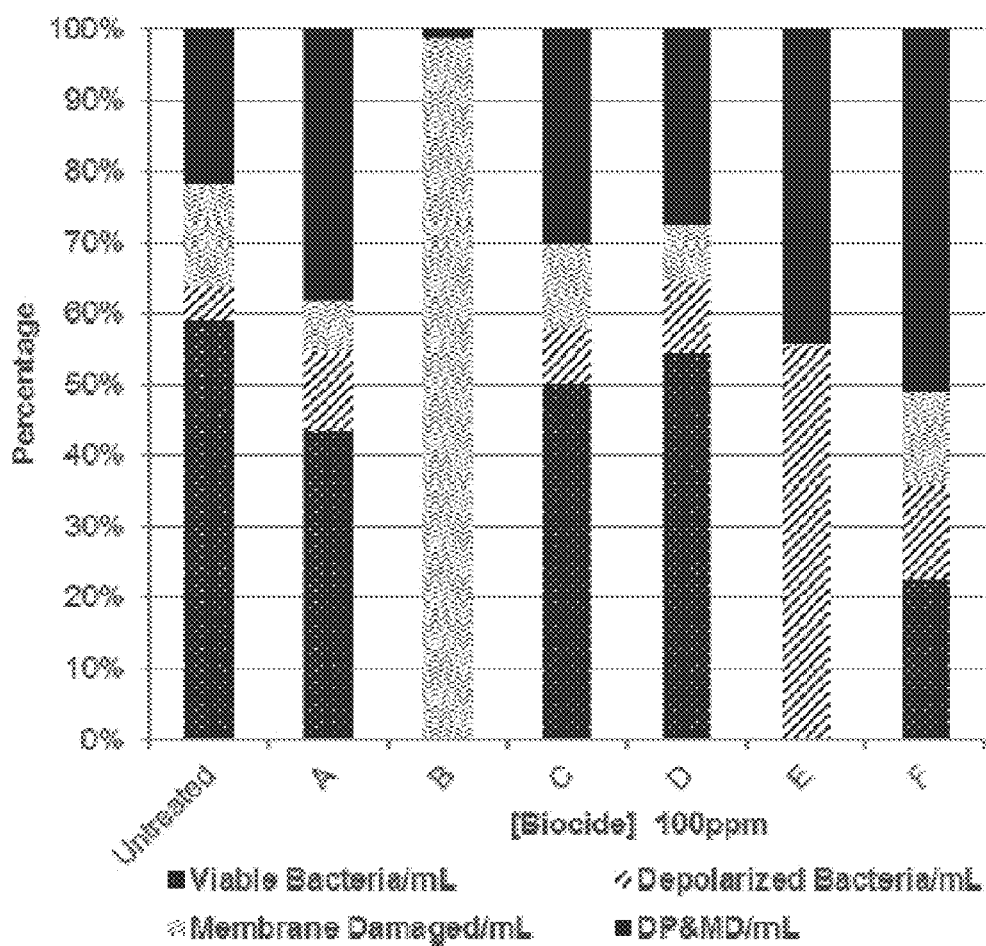
FIG. 9 depicts a bar graph categorizing bacteria in oilfield water after treatment with 100 ppm of biocide.
Figure 10:
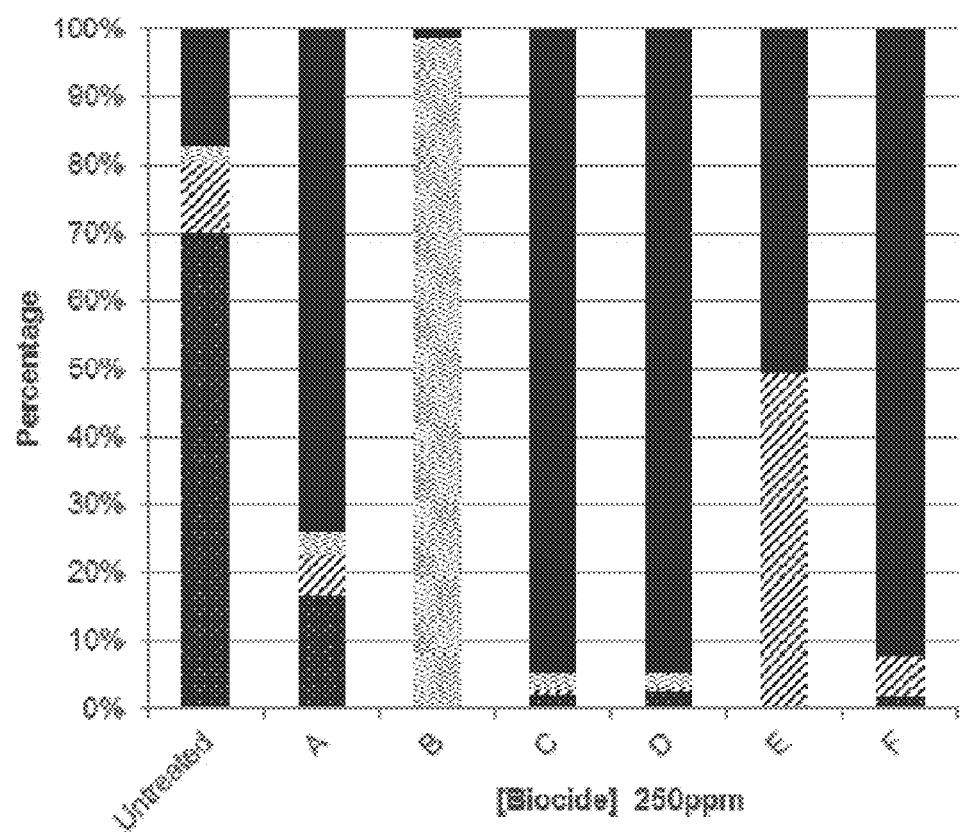
FIG. 10 depicts a bar graph categorizing bacteria in oilfield water after treatment with 250 ppm of biocide.
Figure 11:
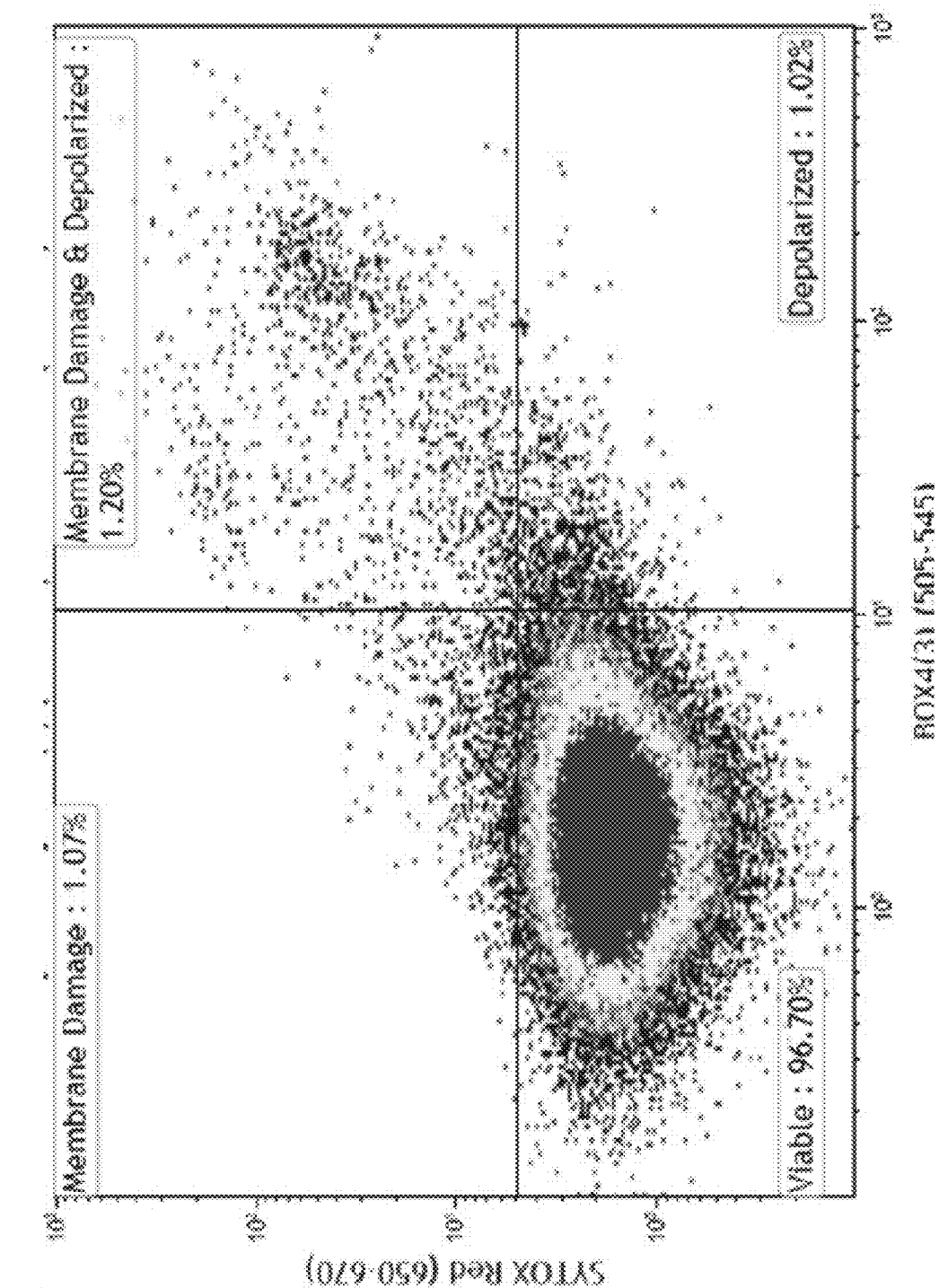
FIG. 11 depicts a bivariate density plot of fluorescence intensity from 650 nm to 670 nm versus fluorescence intensity from 505 nm to 545 nm at [4 hrs].
Figure 12:
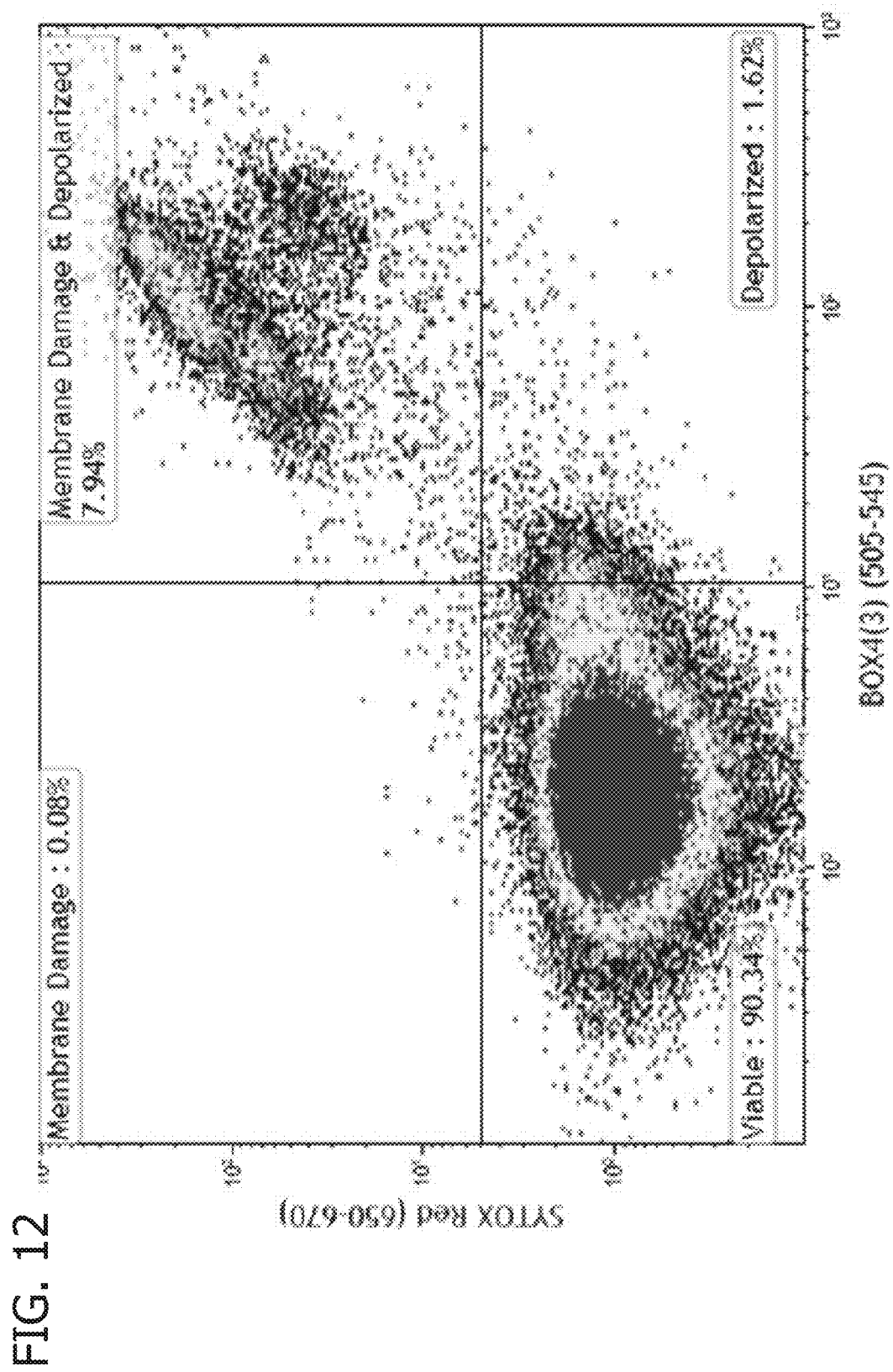
FIG. 12 depicts a bivariate density plot of fluorescence intensity from 650 nm to 670 nm versus fluorescence intensity from 505 nm to 545 nm at [4 hrs].
Figure 13:
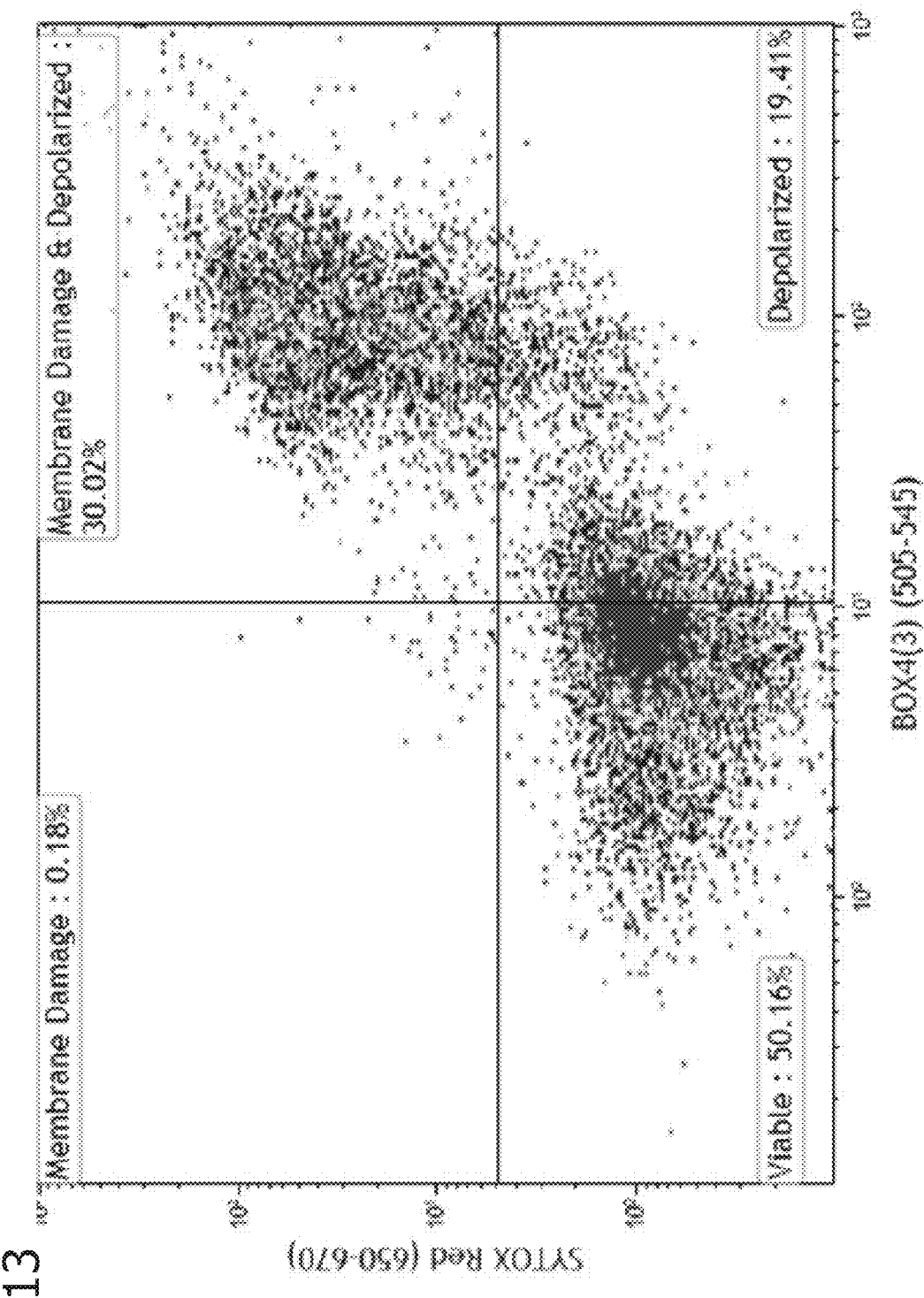
FIG. 13 depicts a bivariate density plot of fluorescence intensity from 650 nm to 670 nm versus fluorescence intensity from 505 nm to 545 nm at [4 hrs].
Figure 14:
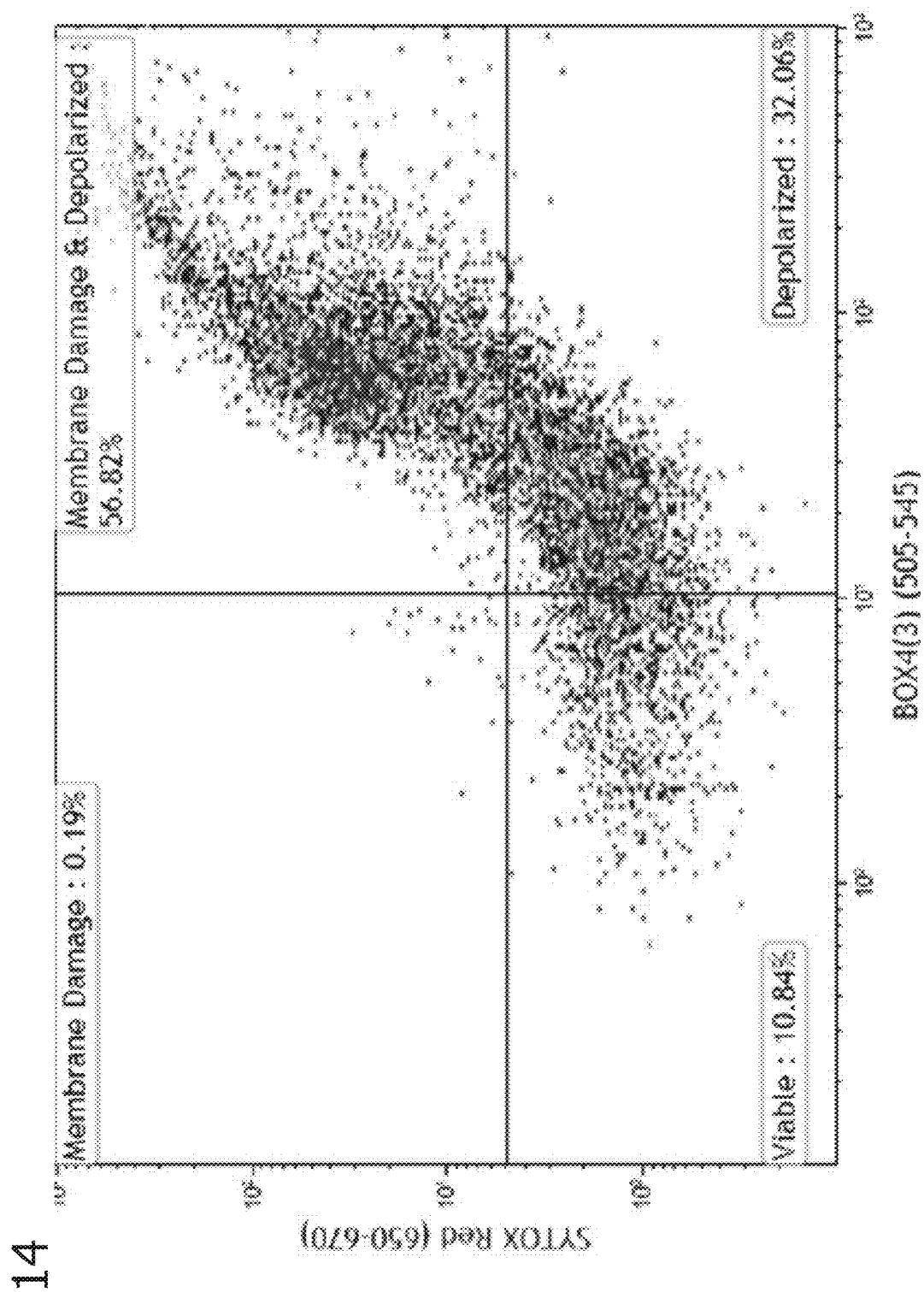
FIG. 14 depicts a bivariate density plot of fluorescence intensity from 650 nm to 670 nm versus fluorescence intensity from 505 nm to 545 nm at [4 hrs].

Oilfield water was treated with the following 6 common biocides in concentrations of 100 ppm and 250 ppm: Biocide A—glutaraldehyde with didecyldimethylammonium chloride; Biocide B—cocodiamine quat; Biocide C—glutaraldehyde; Biocide D—glutaraldehyde with polymer; Biocide E—didecyldimethylammonium chloride; and Biocide F—THPS. Flow cytometry samples were prepared for two untreated oilfield water samples and a sample for each biocide at 100 ppm and 250 ppm as described above in Example 1. Flow cytometry was performed on each of the samples as generally described above in Example 2. The bacteria were categorized as described above in Example 1 and the data are presented in bar graph form in FIGS. 9 (100 ppm) and 10 (250 ppm).

Example 5

Concentration-Dependent Mechanism of Action

*E. coli* in LB media was treated with TTPC at a concentration of 75 ppm, 150 ppm, 300 ppm, 600 ppm, or 1200 ppm.

Figure 15:
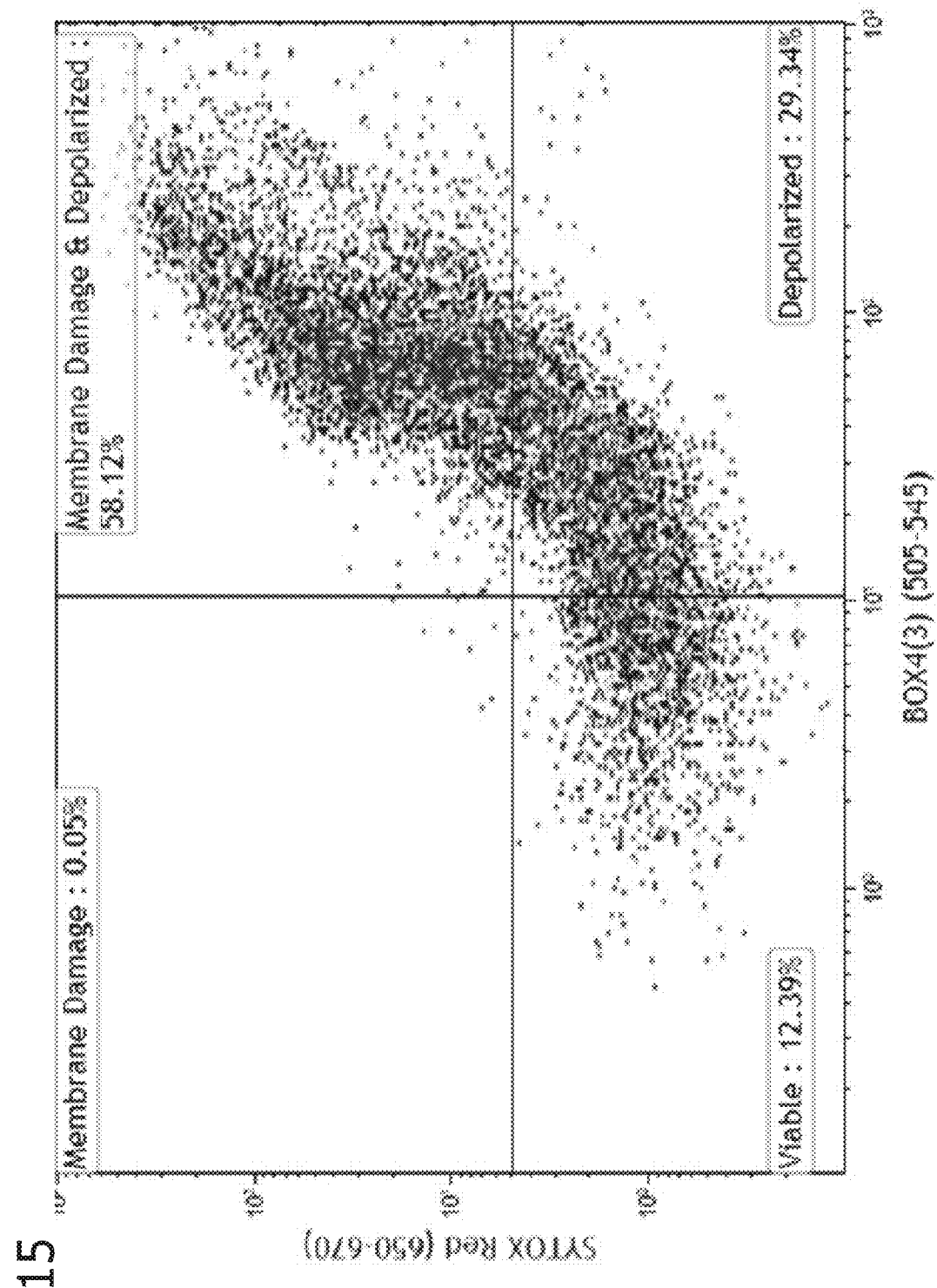
FIG. 15 depicts a bivariate density plot of fluorescence intensity from 650 nm to 670 nm versus fluorescence intensity from 505 nm to 545 nm at [4 hrs].
Figure 16:
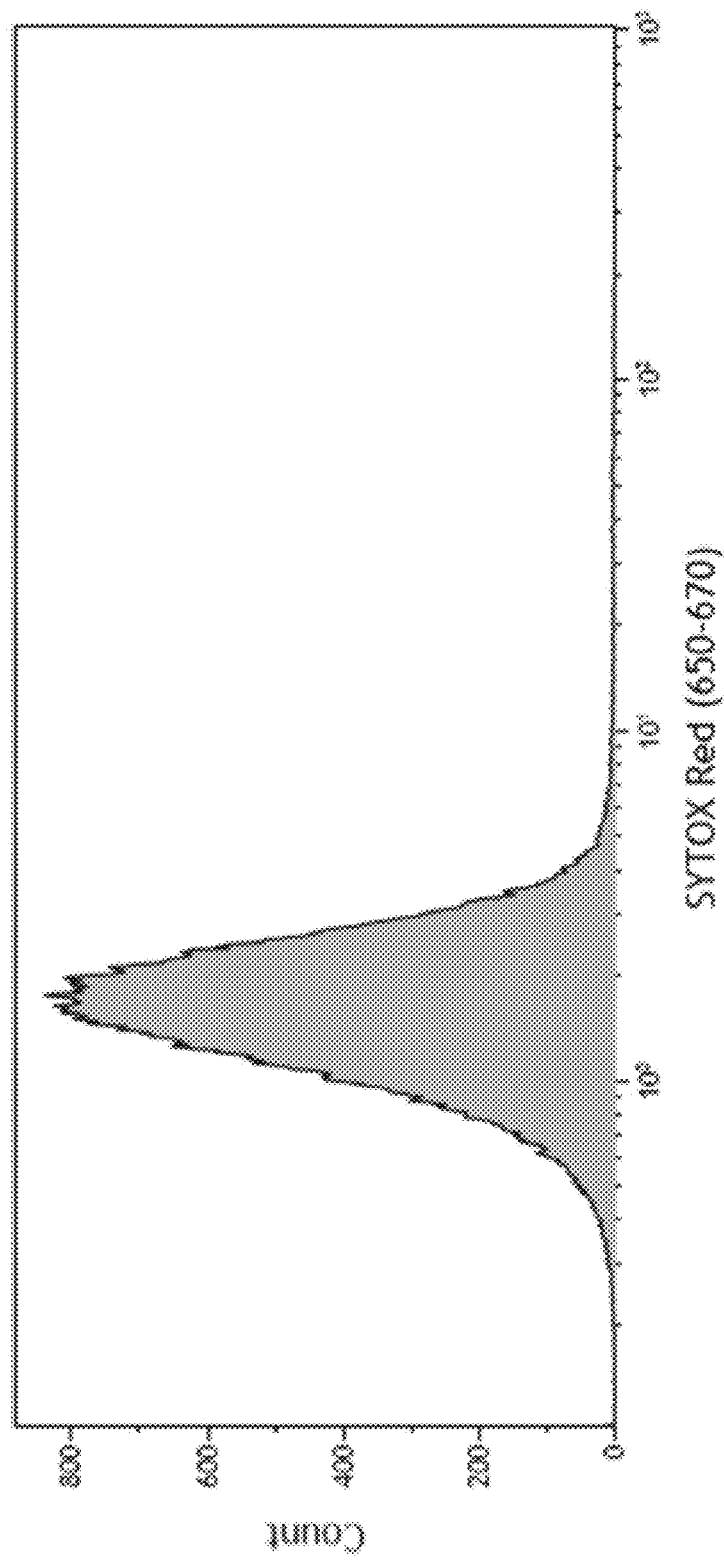
FIG. 16 depicts fluorescence intensity spectrum at a time interval of [4 hrs].
Figure 17:
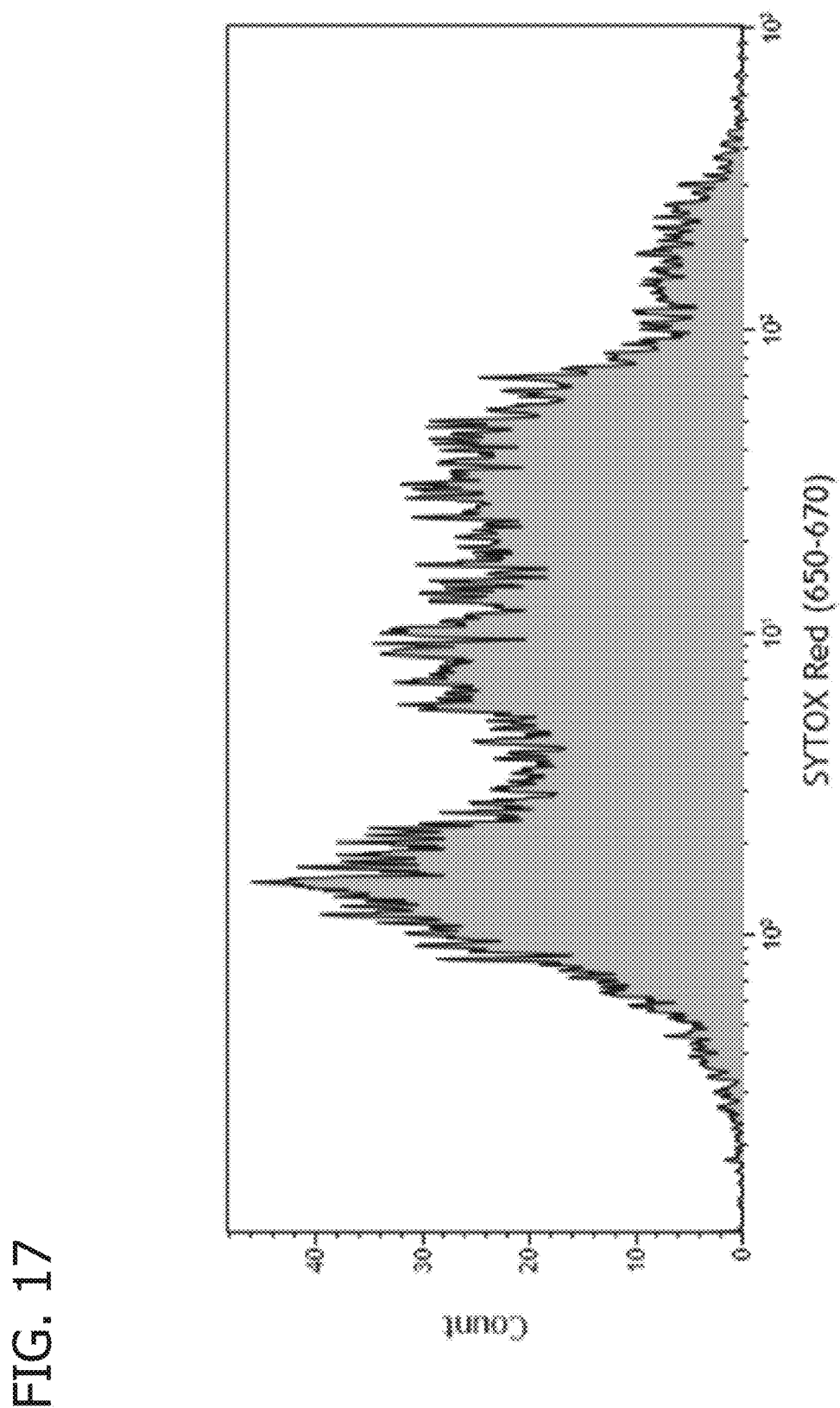
FIG. 17 depicts fluorescence intensity spectrum at a time interval of [4 hrs].
Figure 18:
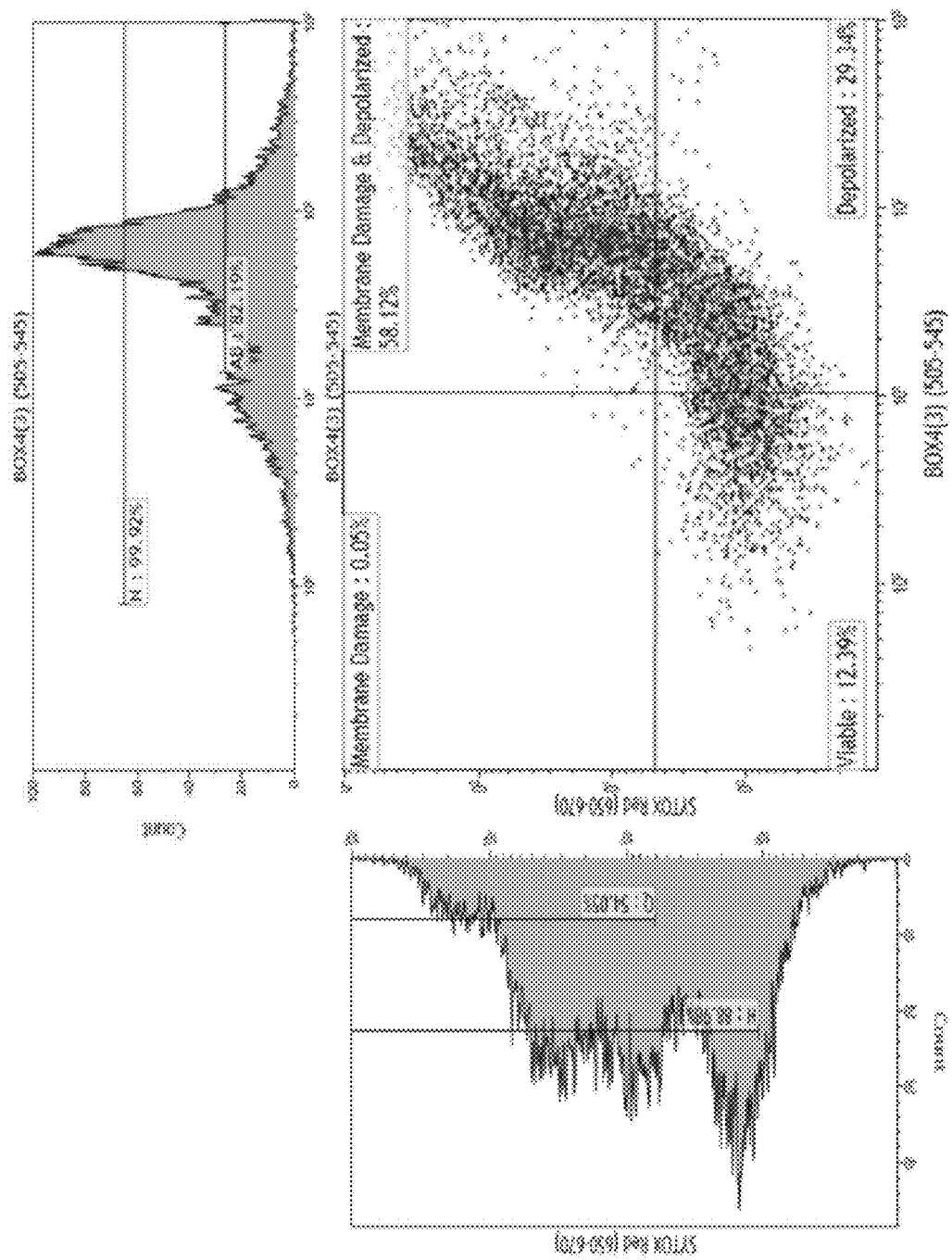
FIG. 18 depicts a bivariate density plot of FIG. 15 flanked by the individual fluorescence spectra from 505 nm to 545 nm (top) and from 650 nm to 670 nm (left).

These samples were prepared into flow cytometry samples as described in Example 1 at a time interval of 4 hours. Flow cytometry was performed on each of the samples as generally described above in Example 2. The data are presented in a bivariate density plot of fluorescence intensity from 650 nm to 670 nm versus fluorescence intensity from 505 nm to 545 nm. Higher fluorescence intensity along the y-axis correlates to more membrane damage and higher fluorescence intensity along the x-axis correlates to greater depolarization. The data from the 75 ppm, 150 ppm, 300 ppm, 600 ppm and 1200 ppm samples are shown in FIGS. 11, 12, 13, 14 and 15, respectively. The fluorescence intensity spectra from 650 nm to 670 nm at a time interval of 2 hours are shown for the 75 ppm and 1200 ppm samples in FIGS. 16 and 17, respectively. The bivariate density plot of FIG. 15 is shown in FIG. 18 flanked by the individual fluorescence spectra from 505 nm to 545 nm (top) and from 650 nm to 670 nm (left).

Example 6

Comparison of Flow Cytometry and Standard Culture Methods

Figure 19A:
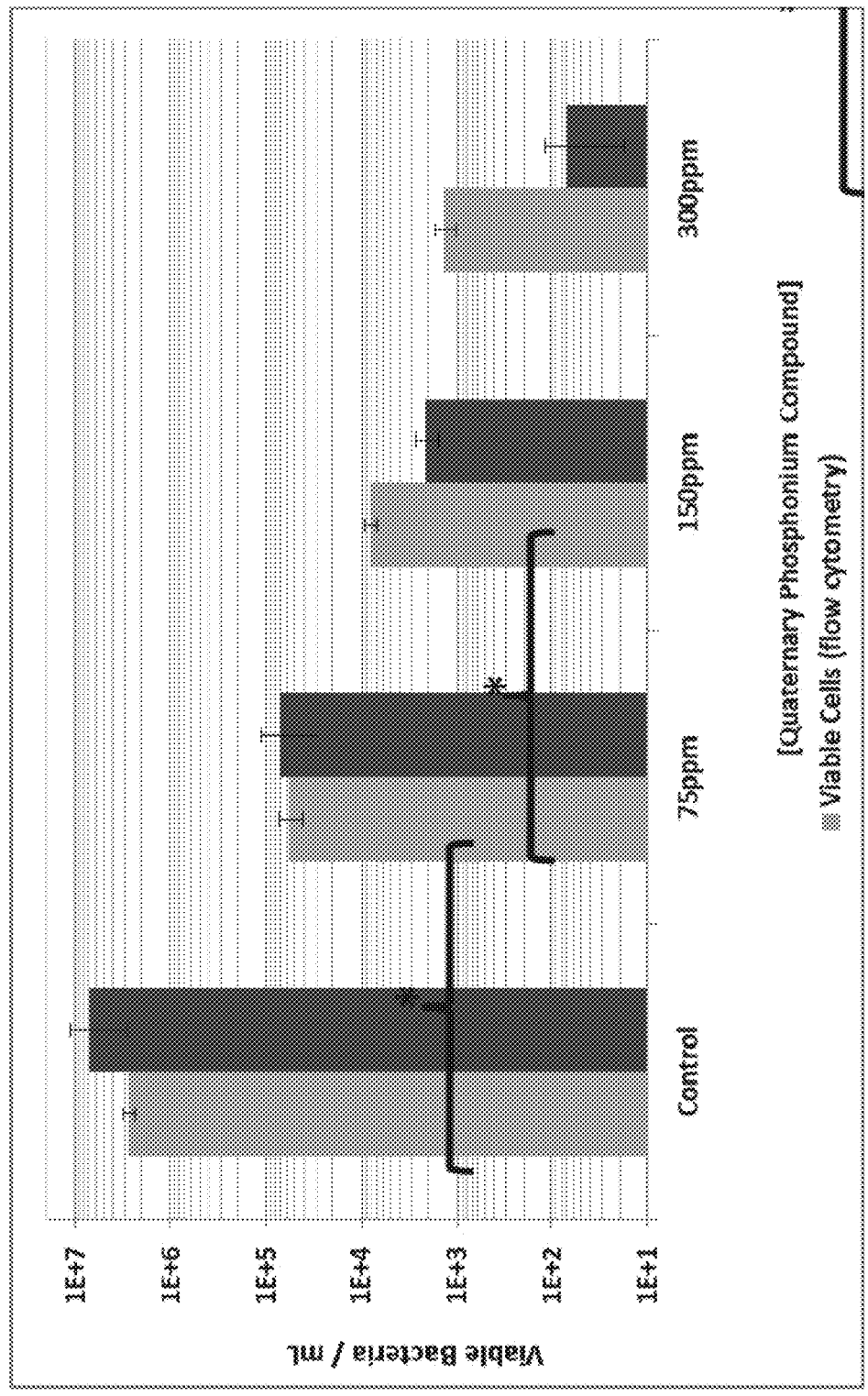
FIG. 19A depicts the number of viable cells as measured by flow cytometry and by standard culture method and FIG. 19B plots the correlation of the standard culture method with the flow cytometry method.

Cultures of *E. coli* were left untreated or treated with tributyltetradecyl phosphonium chloride (TTPC) at 75 ppm, 150 ppm, or 300 ppm. Flow cytometry samples were prepared as described in Example 1 and triplicate culture bottles were prepared of the treated *E. coli* and untreated *E. coli* after 4 hours of incubation at 37° C. The number of viable cells as measured by flow cytometry as described in Examples 2-5 and by a standard culture method involving 9 mL culture bottles serially inoculated by syringe with 1 mL of treated sample is displayed graphically in for 4 hours. Viability was measured by flow cytometry and serial dilution in LB media. As shown in FIG. 19A, flow cytometry showed that the biocide reduced viable bacteria by 97.9%±0.6%, 99.71%±0.04%, and 99.95%±0.01% respectively. Serial dilution culturing showed that the biocide reduced viable bacteria by 99%±0.7%, 99.97%±0.01%, and 99.999%±0.001% respectively. n=3 for flow cytometry and culturing. Error bars indicate 1 standard deviation. An asterisk indicates a statistically significant difference (p<0.05) and two asterisk indicates a p-value <0.01.

Figure 19B:
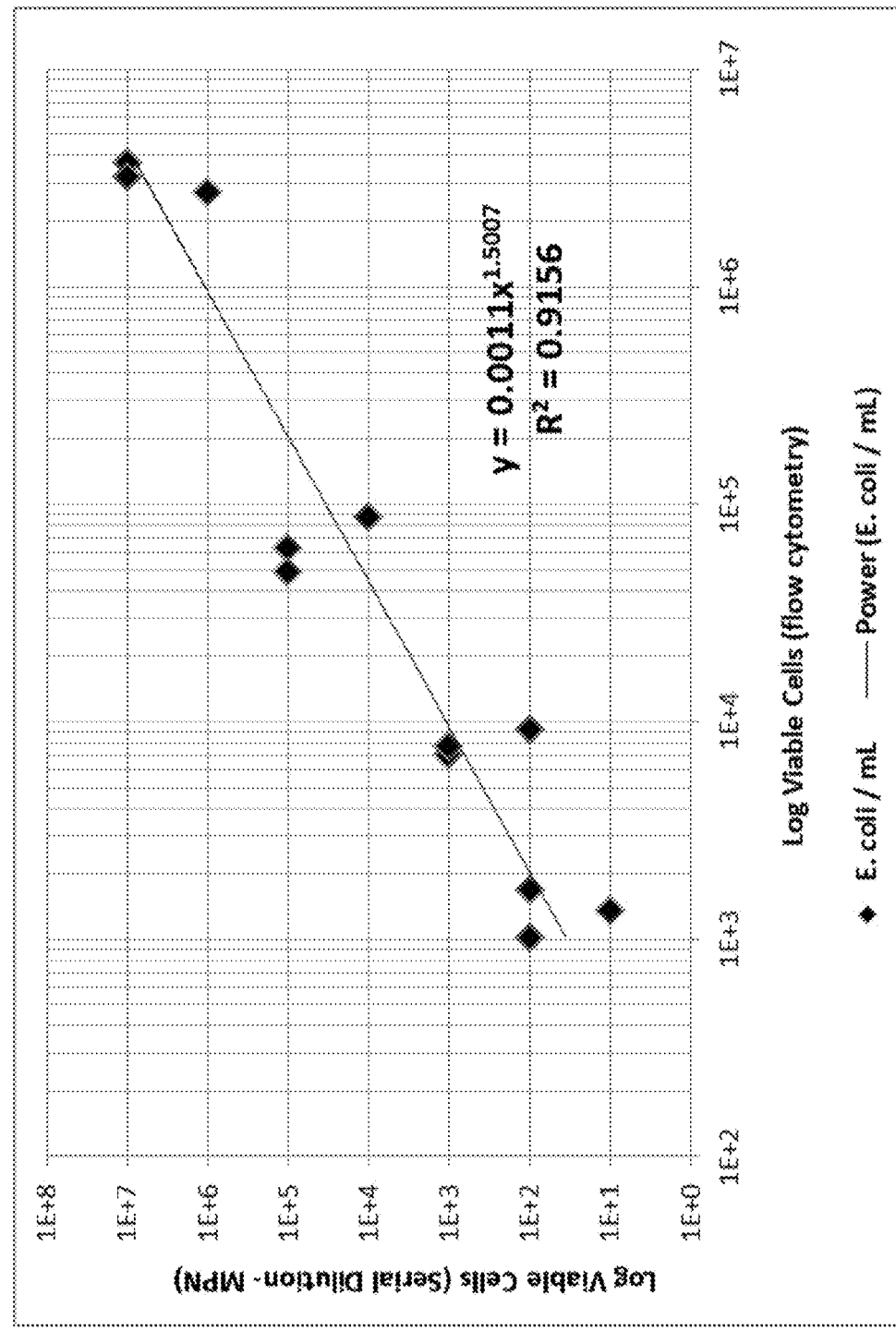

Cultures of *E. coli* were left untreated or treated with tributyltetradecyl phosphonium chloride (TTPC) for 4 hours. Viability was measured by flow cytometry and serial dilution in LB media. Results indicate viability culturing in liquid media closely correlates with flow cytometry viability as measured by membrane permeability and polarization state. As shown in FIG. 19B, a trendline shows the relationship on a logarithmic scale with a $R^2$ value of 0.916.

Example 7

Comparison of Flow Cytometry and ATP Photometry Methods

Figure 20A:
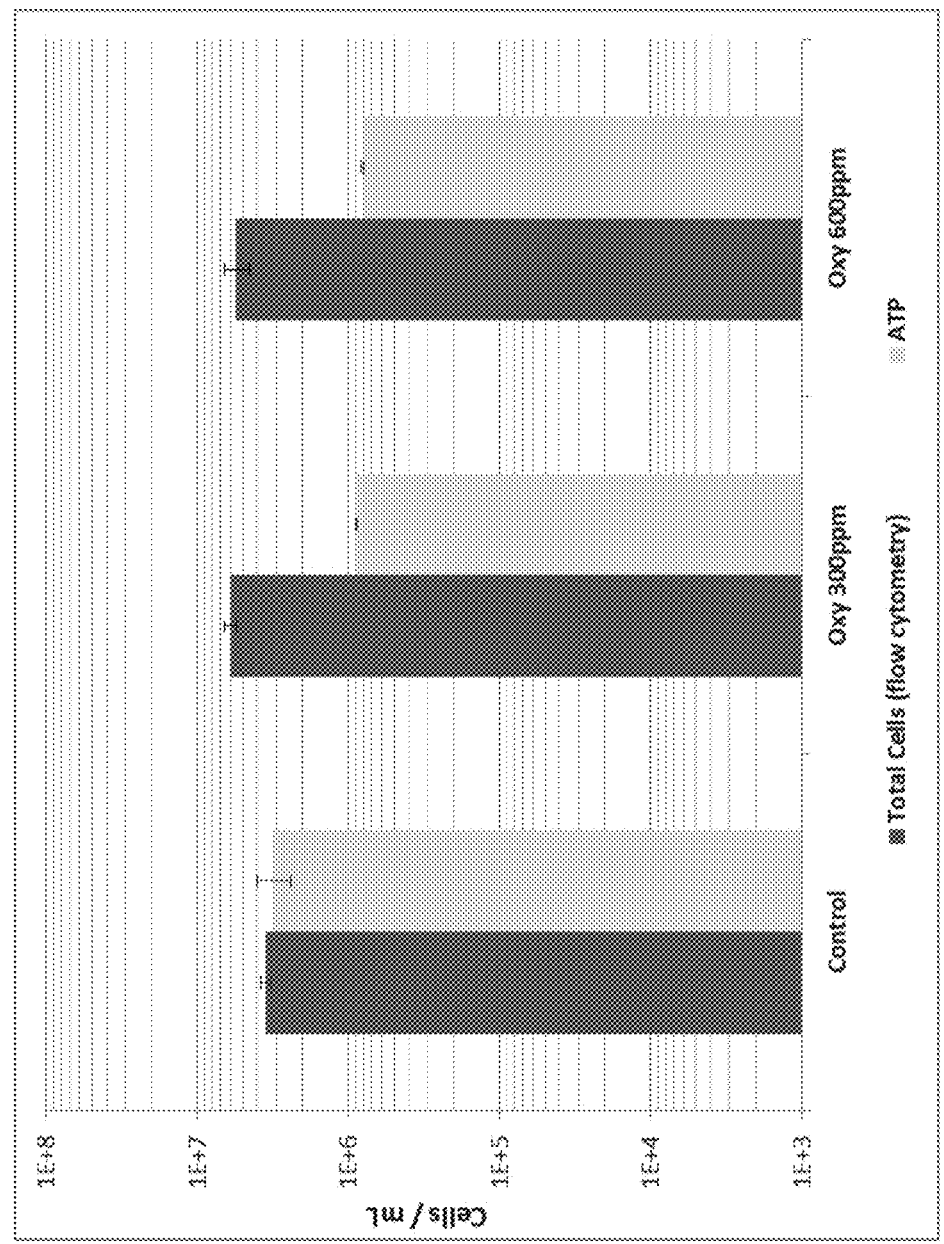
FIGS. 20A, 20B, and 20C depict the number of cells determined by ATP photometry and the number of total cells and viable cells determined by flow cytometry for an untreated sample and samples treated with peracetic acid (Oxy).
Figure 20B:
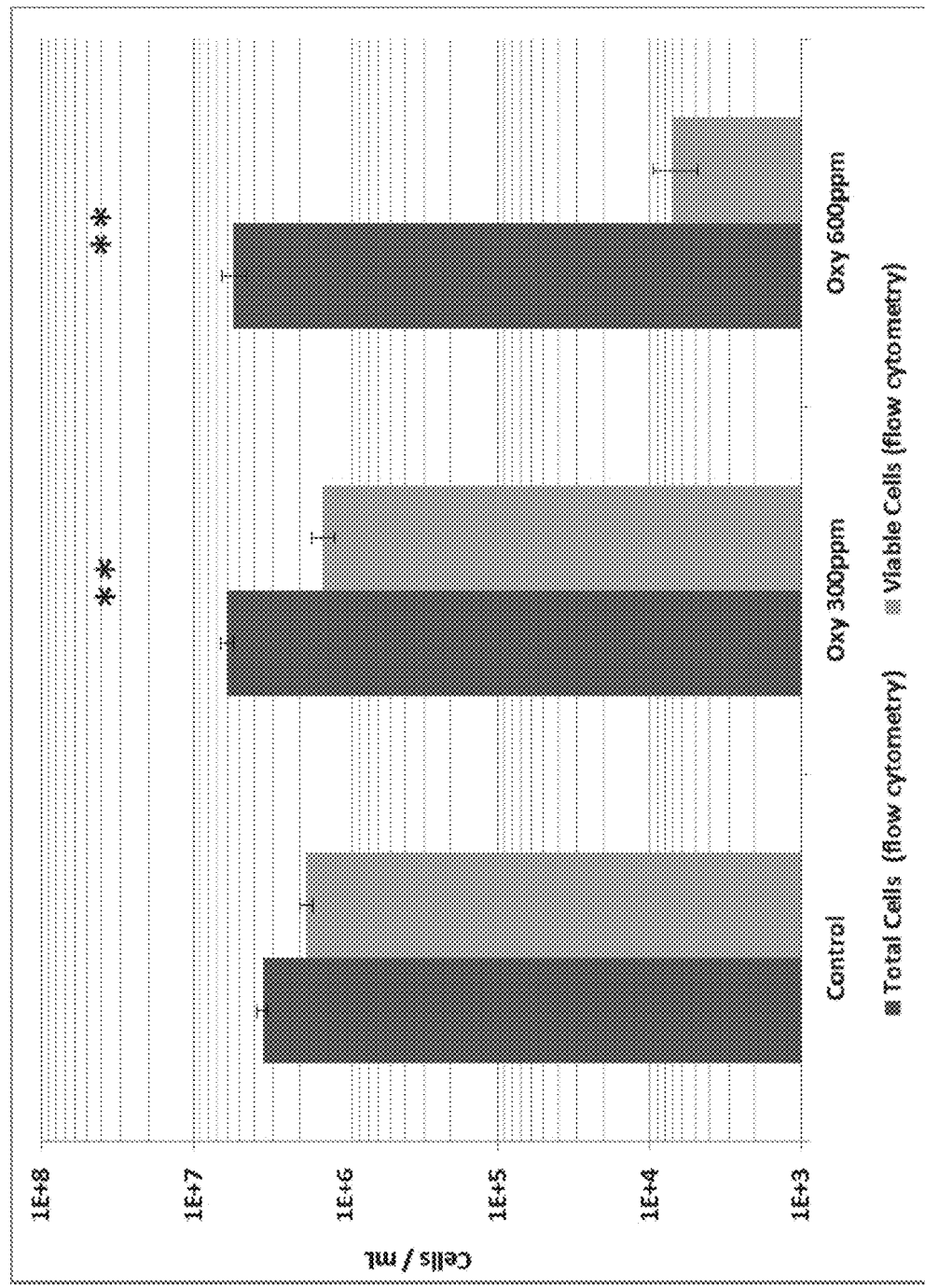
Figure 20C:
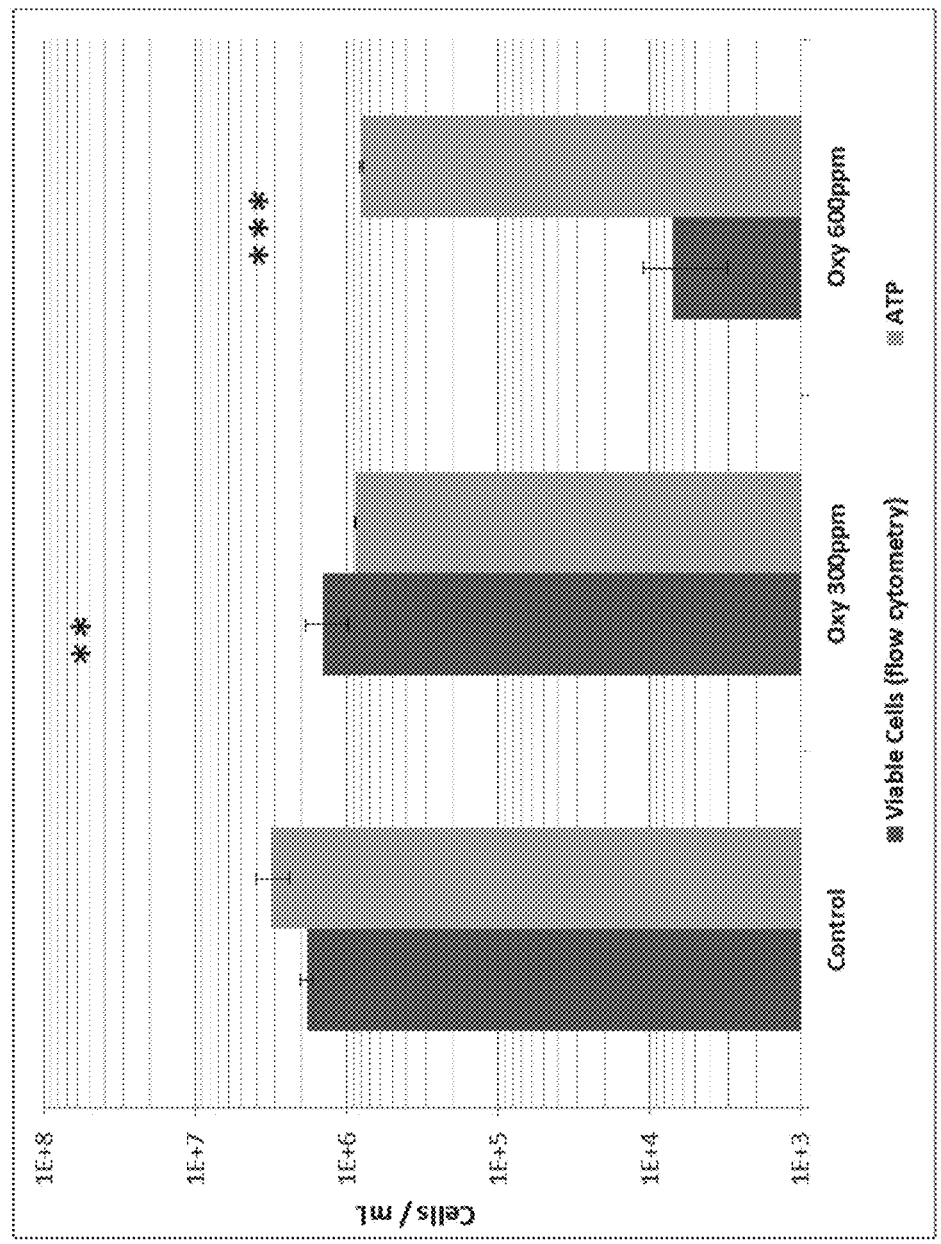

*E. coli* in LB media was treated with peracetic acid (Oxy) at concentrations of 300 ppm (low concentration) and 600 ppm (high concentration). The number of cells was determined by ATP photometry using a luminultra QGA test kit (www.luminultra.com/quench-gone-aqueous-qga.html; the QGA test kit is similar in design to ASTM D4012-81(2009) Standard Test Method for ATP Content of Microorganisms in Water) and the number of total cells and viable cells was determined by flow cytometry as described in Examples 2-5 for an untreated sample and samples treated with peracetic acid in high and low concentrations. The results are shown in bar graph form in FIGS. 20A-20C. The number of cells as determined by ATP photometry more closely correlates with the total cells as determined by flow cytometry than with viable cells as determined by flow cytometry, thus illustrating a significant advantage that the methods described herein possess over ATP photometry.

Example 8

Iron Chelator Treatment

Figure 21A:
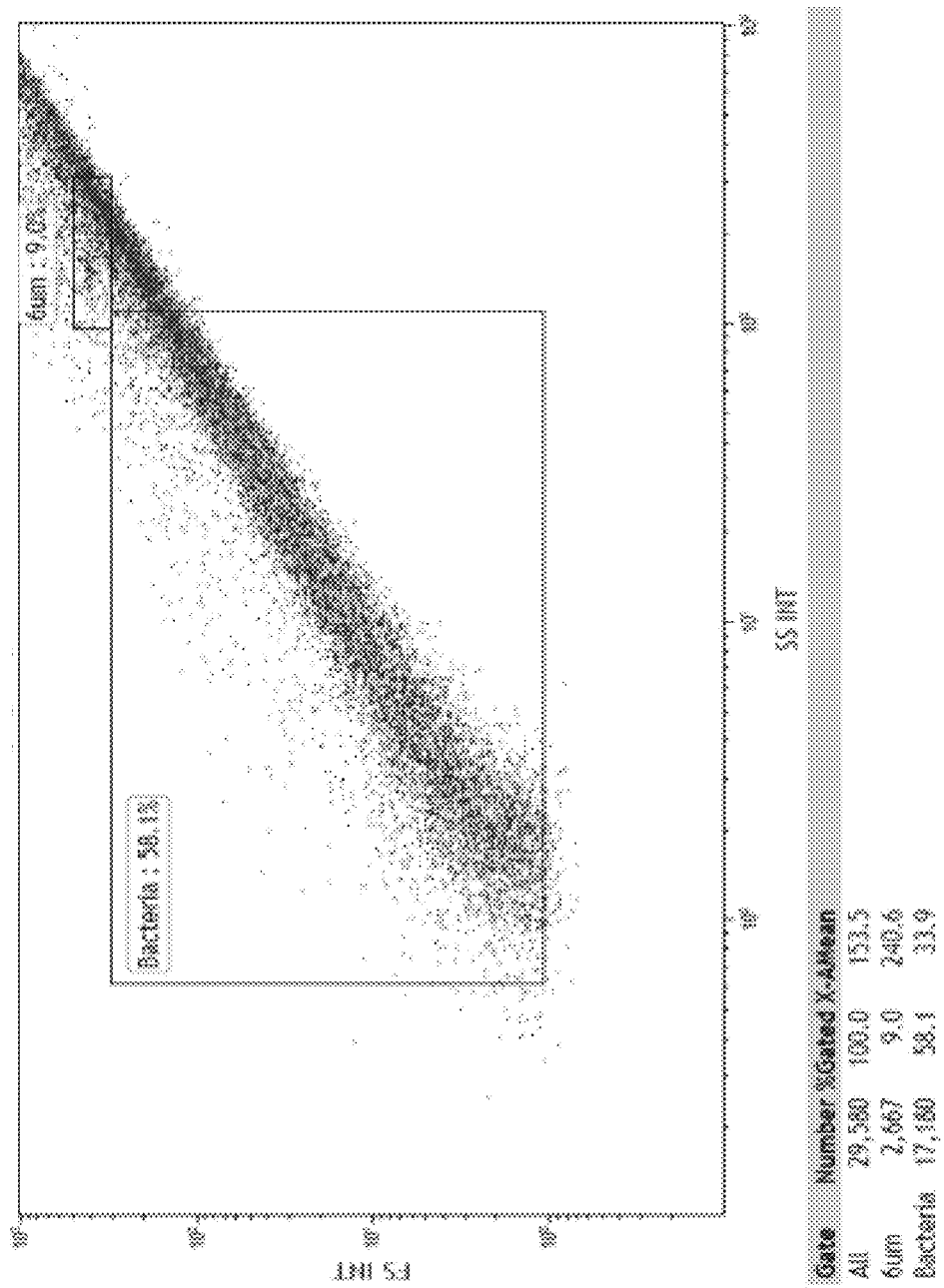
FIGS. 21A and 21B depict a bivariate density plot of fluorescence intensity from 650 nm to 670 nm versus fluorescence intensity from 505 nm to 545 nm at 4 hours for a sample that was untreated with citric acid and for a sample treated with 20 mM citric acid, respectively.
Figure 21B:
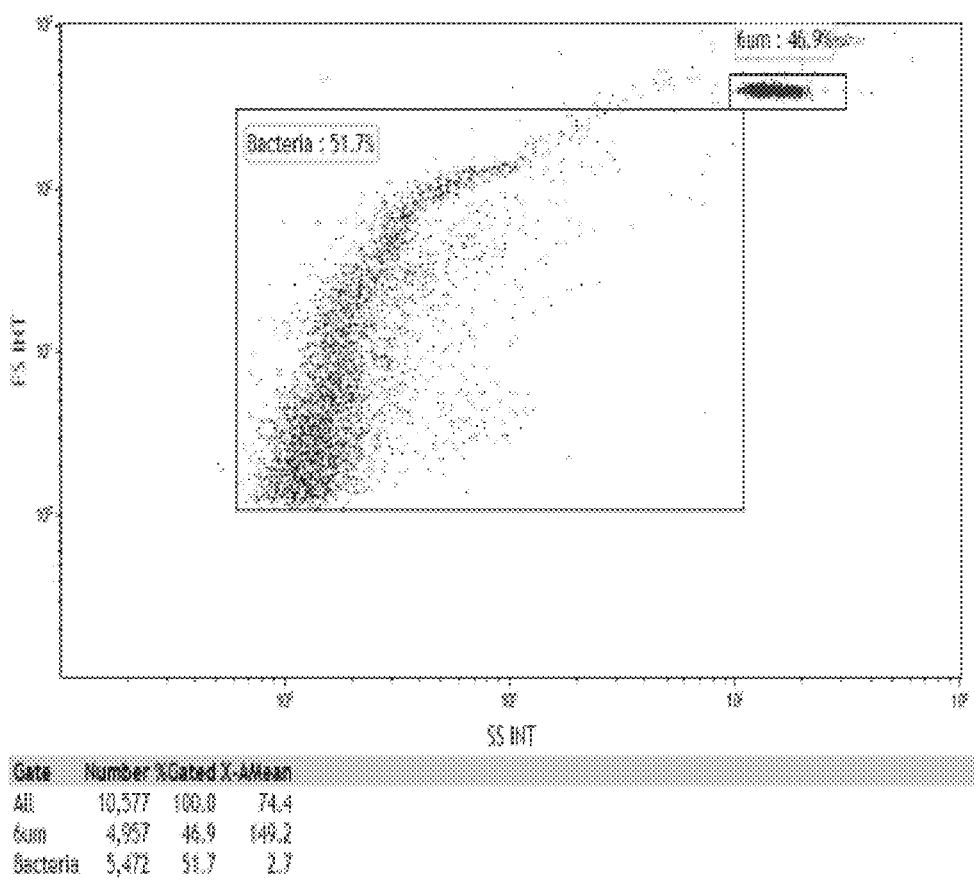

Oilfield water was treated with the iron chelators citric acid and ascorbic acid at concentrations of 5 mM, 10 mM, 20 mM, 30 mM, 40 mM, and 50 mM. Flow cytometry samples were prepared for an untreated oilfield water sample and iron chelator treated oilfield water samples as described above in Example 1. Flow cytometry was performed on each of the samples as generally described above in Example 2. A plot of the forward scattered signal versus the side scattered signal is shown in FIGS. 21A and 21B for citric acid. The enclosed shapes within the plot are visualizations of the respective gates All, 6 um, and Bacteria as described in Example 2. A bar graph visually representing the number of bacterial cells that are viable, membrane damaged, or depolarized at various citric acid concentrations are disclosed in FIG. 22.

Example 9

Effect of Citric Acid Treatment on Flow Cytometry Viable Bacteria

Figure 22:
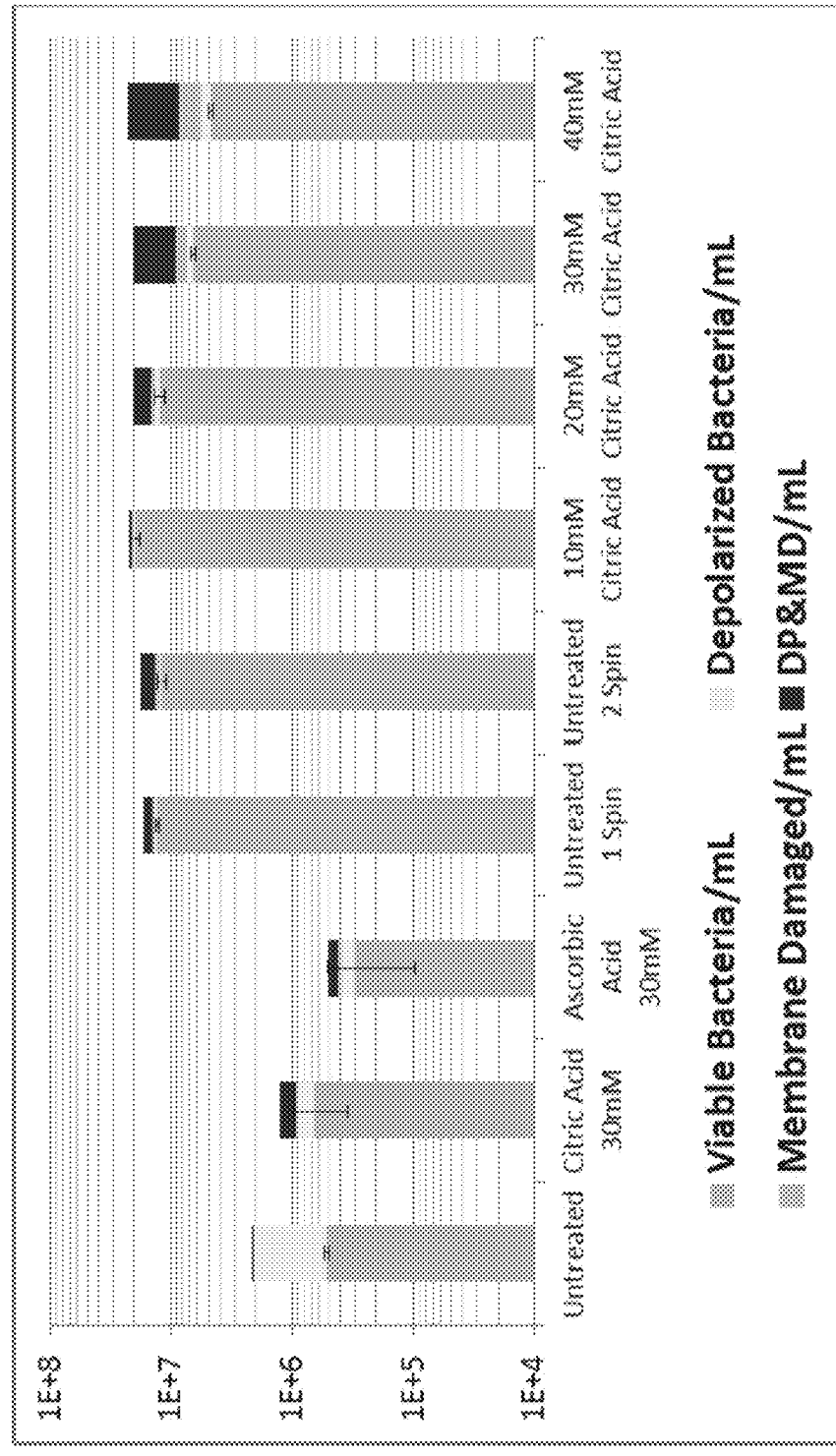
FIG. 22 depicts a bar graph of the results of a flow cytometry study when the sample was treated with citric acid as described in Example 8.
Figure 23:
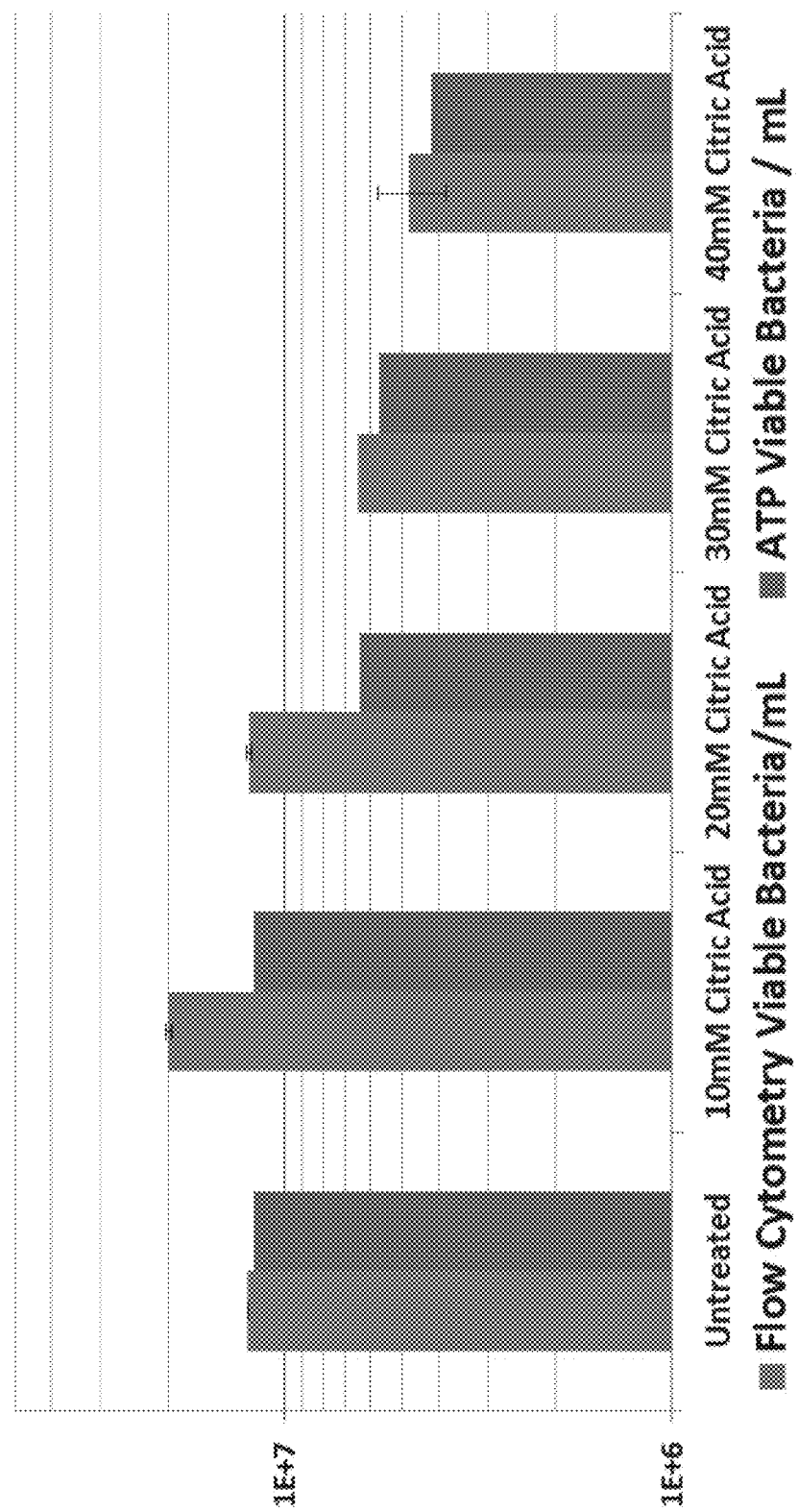
FIG. 23 depicts a bar graph visually representing the number of bacterial cells in the sub-sets of viable cells with differing citric acid concentrations as analyzed by a flow cytometry method and by an ATP testing method.

*E. coli* in LB media was treated with citric acid at concentrations of 10 mM, 20 mM, 30 mM, and 40 mM. Flow cytometry samples were prepared for untreated *E. coli* samples and samples for each citric acid concentration as described above in Example 1. Flow cytometry was performed on each of the samples as generally described above in Example 2. A bar graph visually representing the number of bacterial cells in the sub-set viable bacteria for each flow cytometry sample is compared with viable bacteria results using ATP photometry methods for each sample in FIG. 23. The data in FIGS. 21-23 shows that treatment with citric acid at a concentration less than or equal to 20 mM does not affect the cell viability when analyzed by flow cytometry.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A method of measuring biocide efficacy using flow cytometry, the method comprising:

contacting an oil and gas fluid with at least one biocide and with an iron chelator to reduce interference caused by suspended iron-containing compounds;
performing flow cytometry on the oil and gas fluid; and
determining the mechanism of action or efficacy of the at least one biocide on a microorganism present in the oil and gas fluid.

2. The method of claim 1, wherein the oil and gas fluid contains at least one microorganism.

3. The method of claim 2, wherein the at least one microorganism is prokaryotic, or a eukaryotic.

4. The method of claim 1, wherein at least two biocides are compared for their mechanism of action or efficacy for the purpose of identifying synergy in controlling microorganisms in the oil and gas fluid.

5. The method of claim 1, comprising determining the efficacy of the at least one biocide on a microorganism present in the oil and gas fluid.

6. The method of claim 5, wherein the iron chelator is selected from the group consisting of citric acid, and ascorbic acid.

7. The method of 1, wherein the iron chelator is selected from the group consisting of desferrioxamine, ethylenediaminetetraacetic acid (EDTA), lactoferrin, transferrin, polyacrylic acid, poly(acrylic acid: 2-acrylamido-2-methyl propane sulfonic acid: sulfonated styrene) (Poly-G), sodium hexametaphosphate, citric acid, ascorbic acid, gluconic acid, tartaric acid, oxalic acid, oxalic acid, an organic acid, a phosphonic acid, sodium thiosulfate, and a combination thereof.

8. The method of claim 1, further comprising contacting the microorganism with at least one selectivity agent to produce a labeled microorganism.

9. The method of claim 8, further comprising performing flow cytometry on the labeled microorganism and collecting spectral data for said microorganism.

10. The method of claim 9, further comprising defining one or more subsets of the microorganism based on the spectral data.

11. The method of claim 9, wherein spectral data comprises at least one of forward scattering data, side scattering data, or fluorescence data.

12. The method of claim 11, wherein at least a portion of the spectral data corresponds to a microorganism in a condition selected from the group consisting of viable, membrane-damaged, depolarized, and combinations thereof.

13. The method of claim 8, wherein the at least one selectivity agent is selected from the group consisting of a cell-impermeable stain, a membrane potential stain, and combinations thereof.

14. The method of claim 1, wherein the at least one biocide is selected from the group consisting of aldehydes, dialdehydes, quaternary ammonium compounds, quaternary phosphonium compounds, halogens, and combinations thereof.

15. The method of claim 1, wherein the mechanism of action of the at least one biocide on a microorganism present in the oil and gas fluid is determined.

16. A method of monitoring microorganism growth in an oil and gas fluid, the method comprising:
a) contacting the oil and gas fluid with at least one biocide and with an iron chelator to reduce interference caused by suspended iron-containing compounds;
b) performing flow cytometry on the oil and gas fluid of step a);
c) determining the mechanism of action or efficacy of the at least one biocide on a microorganism present in the oil and gas fluid based on step b);
d) repeating steps (a) to (c) at a later time;
e) comparing results of microorganism growth at step (c) with step (d) to determine if biocide of step (a) is effective in controlling growth of the microorganism in the oil and gas fluid.

17. The method of claim 16, wherein the oil and gas fluid contains at least one microorganism.

18. The method of claim 16, further comprising using alternative biocides in controlling growth of microorganism based upon results in step (e).

19. The method of claim 16, wherein the iron chelator is selected from the group consisting of desferrioxamine, ethylenediaminetetraacetic acid (EDTA), lactoferrin, transferrin, polyacrylic acid, poly(acrylic acid: 2-acrylamido-2-methyl propane sulfonic acid: sulfonated styrene) (Poly-G), sodium hexametaphosphate, citric acid, ascorbic acid, gluconic acid, tartaric acid, oxalic acid, oxalic acid, an organic acid, a phosphonic acid, sodium thiosulfate, and a combination thereof.

20. The method of claim 16, wherein a mechanism of action of the at least one biocide on a microorganism present in the oil and gas fluid is determined.

* * * * *